United States Patent
Staelens et al.

(10) Patent No.: US 11,414,481 B2
(45) Date of Patent: Aug. 16, 2022

(54) SERUM ALBUMIN BINDERS

(71) Applicant: Ablynx N.V., Ghent-Zwijnaarde (BE)

(72) Inventors: Stephanie Staelens, Wevelgem (BE); Soren Steffensen, Etterbeek (BE); Erika Morizzo, Ghent (BE); An Cerdobbel, Nevele (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 16/477,918

(22) PCT Filed: Jan. 17, 2018

(86) PCT No.: PCT/EP2018/051083
§ 371 (c)(1),
(2) Date: Jul. 15, 2019

(87) PCT Pub. No.: WO2018/134235
PCT Pub. Date: Jul. 26, 2018

(65) Prior Publication Data
US 2019/0367597 A1    Dec. 5, 2019

Related U.S. Application Data

(60) Provisional application No. 62/446,988, filed on Jan. 17, 2017.

(51) Int. Cl.
| | |
|---|---|
| *C12P 21/06* | (2006.01) |
| *C12N 5/02* | (2006.01) |
| *C12N 5/20* | (2006.01) |
| *C07K 16/46* | (2006.01) |
| *C07K 16/00* | (2006.01) |
| *C07H 21/04* | (2006.01) |
| *C07K 16/18* | (2006.01) |
| *A61K 39/00* | (2006.01) |

(52) U.S. Cl.
CPC ........ *C07K 16/18* (2013.01); *A61K 2039/505* (2013.01); *C07K 2317/22* (2013.01); *C07K 2317/24* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2013/0129727 A1 | 5/2013 | Zhang et al. | |
| 2014/0186365 A1 | 7/2014 | Robinson et al. | |
| 2019/0367596 A1 | 12/2019 | Staelens et al. | |
| 2019/0367598 A1* | 12/2019 | Staelens ................. | C07K 16/18 |

FOREIGN PATENT DOCUMENTS

| | | | |
|---|---|---|---|
| JP | 2010-502208 A | 1/2010 | |
| JP | 2010-518062 A | 5/2010 | |
| JP | 2012-503638 A | 2/2012 | |
| JP | 2012-532620 A | 12/2012 | |
| JP | 2013-506628 A | 2/2013 | |
| JP | 2013-538566 A | 10/2013 | |
| JP | 2014-520129 A | 8/2014 | |
| JP | 2014-193869 A | 10/2014 | |
| RU | 2464276 C2 | 10/2012 | |
| WO | WO 2006/122787 A1 | 11/2006 | |
| WO | WO 2007/063311 A2 | 6/2007 | |
| WO | WO 2008/028977 A2 | 3/2008 | |
| WO | WO 2008/096158 A2 | 8/2008 | |
| WO | WO 2010/035012 A1 | 4/2010 | |
| WO | WO 2011/006915 A2 | 1/2011 | |
| WO | WO 2011/039096 A1 | 4/2011 | |
| WO | WO 2012/020143 A1 | 2/2012 | |
| WO | WO 2012/022703 A2 | 2/2012 | |
| WO | WO 2012/175400 A1 | 12/2012 | |
| WO | WO 2014/037419 A1 | 3/2014 | |
| WO | WO 2014/111550 A1 | 7/2014 | |
| WO | WO 2016/180969 A1 | 11/2016 | |
| WO | WO 2017/089618 A1 | 6/2017 | |

OTHER PUBLICATIONS

Holt et al. Anti-serum albumin domain antibodies forextending the half-lives of short lived drugs. Protein Engineering, Design & Selection vol. 21 No. 5 pp. 283-288, 2008. (Year: 2008).*
Beirnaert et al. Bivalent Llama Single-Domain Antibody Fragments against Tumor Necrosis Factor Have Picomolar Potencies due to Intramolecular Interactions. Frontiers in Immunology. 2017, 8:867. (Year: 2017).*
Steeland et al. Generation and Characterization of Small Single Domain Antibodies Inhibiting Human Tumor Necrosis Factor Receptor 1. RNAL of Biological Chemistry vol. 290, No. 7, pp. 4022-4037, Feb. 13, 2015. (Year: 2015).*
Strohl, W.R. Fusion Proteins for Half-Life Extension of Biologies as a Strategy to Make Biobetters. BioDrugs (2015) 29:215-239. (Year: 2015).*
PCT/EP2018/051083, Apr. 24, 2018, International Search Report and Written Opinion.
PCT/EP2018/051083, Aug. 1, 2019, International Preliminary Report on Patentability.

(Continued)

*Primary Examiner* — Maher M Haddad
(74) *Attorney, Agent, or Firm* — Wolf, Greenfield & Sacks, P.C.

(57) ABSTRACT

The present invention relates to amino acid sequences that can bind to serum albumin. In particular, the present invention relates to immunoglobulin single variable domains, and in particular heavy-chain immunoglobulin single variable domains, that can bind to serum albumin. The invention also relates to proteins, polypeptides and other constructs, compounds, molecules or chemical entities that comprise at least one of the immunoglobulin single variable domains binding to serum albumin that are described herein.

22 Claims, 15 Drawing Sheets

Specification includes a Sequence Listing.

(56) References Cited

OTHER PUBLICATIONS

Kang et al, Isolation of human anti-serum albumin Fab antibodies with an extended serum-half life. Immunol Lett. Jan. 2016;169:33-40. doi: 10.1016/j.imlet.2015.11.013. Epub Nov. 22, 2015.
Brevini et al., No shortcuts to pig embryonic stem cells. Theriogenology. Sep. 1, 2010;74(4):544-50. doi: 10.1016/j.theriogenology.2010.04.020. Epub Jun. 8, 2010.
Cao et al., Isolation and culture of primary bovine embryonic stem cell colonies by a novel method. J Exp Zool A Ecol Genet Physiol. Jun. 1, 2009;311(5):368-76. doi: 10.1002/jez.535.
Colman, Effects of amino acid sequence changes on antibody-antigen interactions. Res Immunol. Jan. 1994;145(1):33-6. doi: 10.1016/s0923-2494(94)80039-1.
Houdebine, Methods to Generate Transgenic Animals. From Genetic Engineering in Livestock. Eds Engelhard et al. Springer-Verlag Berlin Heidelberg. 2009:31-48. 20 pages.
Paris et al., Equine embryos and embryonic stem cells: defining reliable markers of pluripotency. Theriogenology. Sep. 1, 2010;74(4):516-24. doi: 10.1016/j.theriogenology.2009.11.020. Epub Jan. 13, 2010.
Rudikoff et al., Single amino acid substitution altering antigen-binding specificity. Proc Natl Acad Sci U S A. Mar. 1982;79(6):1979-83. doi: 10.1073/pnas.79.6.1979.
U.S. Appl. No. 16/465,188, filed May 30, 2019, Staelens et al.
U.S. Appl. No. 16/477,927, filed Jul. 15, 2019, Staelens et al.
PCT/EP2017/081818, Mar. 13, 2018, International Search Report and Written Opinion.
PCT/EP2017/081818, Jun. 20, 2019, International Preliminary Report on Patentability.
PCT/EP2018/051082, Mar. 28, 2018, International Search Report and Written Opinion.
PCT/EP2018/051082, Aug. 1, 2019, International Preliminary Report on Patentability.
Alaoui-Ismaili et al., Design of second generation therapeutic recombinant bone morphogenetic proteins. Cytokine Growth Factor Rev. Oct.-Dec. 2009;20(5-6):501-7. doi: 10.1016/j.cytogfr.2009.10.001. Epub Nov. 11, 2009.
Bowie et al., Deciphering the message in protein sequences: tolerance to amino acid substitutions. Science. Mar. 16, 1990;247(4948):1306-10. doi: 10.1126/science.2315699.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38. doi: 10.1083/jcb.111.5.2129.
Casset et al., A peptide mimetic of an anti-CD4 monoclonal antibody by rational design. Biochem Biophys Res Commun. Jul. 18, 2003;307(1):198-205. doi: 10.1016/s0006-291x(03)01131-8.
Chen et al., Selection and analysis of an optimized anti-VEGF antibody: crystal structure of an affinity-matured Fab in complex with antigen. J Mol Biol. Nov. 5, 1999;293(4):865-81. doi: 10.1006/jmbi.1999.3192.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84. doi: 10.4049/jimmunol.169.6.3076.
Dockal et al., The three recombinant domains of human serum albumin. Structural characterization and ligand binding properties. J Biol Chem. Oct. 8, 1999;274(41):29303-10.
Guo et al., Protein tolerance to random amino acid change. Proc Natl Acad Sci U S A. Jun. 22, 2004;101(25):9205-10. doi: 10.1073/pnas.0403255101. Epub Jun. 14, 2004.
Holm et al., Functional mapping and single chain construction of the anti-cytokeratin 8 monoclonal antibody TS1. Mol Immunol. Feb. 2007;44(6):1075-84. doi: 10.1016/j.molimm.2006.08.001. Epub Sep. 20, 2006.
MacCallum et al., Antibody-antigen interactions: contact analysis and binding site topography. J Mol Biol. Oct. 11, 1996;262(5):732-45. doi: 10.1006/jmbi.1996.0548.
Nurdiansyah et al., A comparative analysis of serum albumin from different species to determine a natural source of albumin that might be useful for human therapy. J Taibah Univ Med Sci. 2016;11(3):243-249.
Pawson et al., Assembly of cell regulatory systems through protein interaction domains. Science. Apr. 18, 2003;300(5618):445-52. doi: 10.1126/science.1083653.
Riechmann et al., Single domain antibodies: comparison of camel VH and camelised human VH domains. J Immunol Methods. Dec. 10, 1999;231(1-2):25-38. doi: 10.1016/s0022-1759(99)00138-6.
Vajdos et al., Comprehensive functional maps of the antigen-binding site of an anti-ErbB2 antibody obtained with shotgun scanning mutagenesis. J Mol Biol. Jul. 5, 2002;320(2):415-28. doi: 10.1016/S0022-2836(02)00264-4.
Wu et al., Humanization of a murine monoclonal antibody by simultaneous optimization of framework and CDR residues. J Mol Biol. Nov. 19, 1999;294(1):151-62. doi: 10.1006/jmbi.1999.3141.

* cited by examiner

Figure 1

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | -- |
| 110 | 110 | 146 | -- |
| 112 | 112 | 148 | -- |

Source: http://www.bioc.uzh.ch/plueckthun/antibody/Numbering/NumFrame.html

Figure 2

| SEQ ID NO | Description | Sequence |
|---|---|---|
| 1 | Reference | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 2 | Reference | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| 3 | CDR1 (Kabat) | SFGMS |
| 4 | CDR2 (Kabat) | SISGSGSDTLYADSVKG |
| 5 | CDR3 (Kabat/Abm) | GGSLSR |
| 6 | CDR1 (Abm) | GFTFRSFGMS |
| 7 | CDR2 (Abm) | SISGSGSDTL |
| 8 | CDR3 (Kabat/Abm) | GGSLSR |
| 9 | CDR1 (Kabat) | TYVMG |
| 10 | CDR2 (Kabat) | AISQNSIHTYYANSVKG |
| 11 | CDR2 (Kabat)) | AISQNSIHTYYADSVKG |
| 12 | CDR1 (Abm) | GGTFSTYVMG |
| 13 | CDR2 (Abm) | AISQNSIHTY |
| 14 | CDR3 (Kabat/Abm) | SRFTSWYTADYEYDY |
| 15 | C-terminal sequence | VTVSS |
| 16 | 15GS linker | GGGGSGGGGSGGGGS |
| 17 | 35 GS linker | GGGGSGGGGSGGGGSGGGGSGGGGSGGGGSGGGGS |

Figure 2 (continued)

| SEQ ID NO | Description | Sequence |
|---|---|---|
| 18 | Invention | EVQLVESGGGLVQTGDSLRLSCAASGGTFSTYVMGWFRQAPGKEREFVSAISQNSIHTYYANSVKGRFTISRDNDKNTVYLQLNSLKPEDTAVYYCAASRFTSWYTADYEYDYWGQGTLVTVSS |
| 19 | Invention | EVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSS |
| 20 | Invention | EVQLVESGGGVVQPGGSLRLSCAASGGTFSTYVMGWFRQAPGKEREFVSAISQNSIHTYYADSVKGRFTISRDNSKNTVYLQLNSLRPEDTALYYCAASRFTSWYTADYEYDYWGQGTLVTVSS |
| 21 | Invention | EVQLVESGGGVVQPGGSLRLSCAASGGTFSTYVMGWFRQAPGKEREFVSAISQNSIHTYYANSVKGRFTISRDNSKNTVYLQMNSLRPEDTALYYCAASRFTSWYTADYEYDYWGQGTLVTVSS |
| 22 | Invention | EVQLVESGGGVVQPGGSLRLSCAASGGTFSTYVMGWFRQAPGKEREFVSAISQNSIHTYYADSVKGRFTISRDNSKNTVYLQMNSLRPEDTALYYCAASRFTSWYTADYEYDYWGQGTLVTVSS |
| 23 | Invention | EVQLVESGGGVVQPGGSLRLSCAASGGTFSTYVMGWFRQAPGKEREFVAAISQNSIHTYYANSVKGRFTISRDNSKNTVYLQLNSLRPEDTALYYCAASRFTSWYTADYEYDYWGQGTLVTVSS |
| 24 | Invention | EVQLVESGGGVVQPGGSLRLSCAASGGTFSTYVMGWFRQAPGKEREFVAAISQNSIHTYYADSVKGRFTISRDNSKNTVYLQLNSLRPEDTALYYCAASRFTSWYTADYEYDYWGQGTLVTVSS |
| 25 | Invention | EVQLVESGGGVVQPGGSLRLSCAASGGTFSTYVMGWFRQAPGKEREFVAAISQNSIHTYYANSVKGRFTISRDNSKNTVYLQMNSLRPEDTALYYCAASRFTSWYTADYEYDYWGQGTLVTVSS |
| 26 | Invention | EVQLVESGGGVVQPGGSLRLSCAASGGTFSTYVMGWFRQAPGKEREFVAAISQNSIHTYYADSVKGRFTISRDNSKNTVYLQMNSLRPEDTALYYCAASRFTSWYTADYEYDYWGQGTLVTVSS |

Figure 2 (continued)

| SEQ ID NO | Description | Sequence |
|---|---|---|
| 27 | Invention | EVQLVESGGGLVQTGDSLRLSCAASGGTFSTYVMGWFRQAPGKEREFVSAISQNSIHTYYANSVKGRFTISRDNDKNTVYLQLNSLKPEDTAVYYCAASRFTSWYTADYEYDYWGQGTLVTVSSA |
| 28 | Invention | EVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSA |
| 29 | Invention | EVQLVESGGGVVQPGGSLRLSCAASGGTFSTYVMGWFRQAPGKEREFVSAISQNSIHTYYADSVKGRFTISRDNSKNTVYLQLNSLRPEDTALYYCAASRFTSWYTADYEYDYWGQGTLVTVSSA |
| 30 | Invention | EVQLVESGGGVVQPGGSLRLSCAASGGTFSTYVMGWFRQAPGKEREFVSAISQNSIHTYYANSVKGRFTISRDNSKNTVYLQMNSLRPEDTALYYCAASRFTSWYTADYEYDYWGQGTLVTVSSA |
| 31 | Invention | EVQLVESGGGVVQPGGSLRLSCAASGGTFSTYVMGWFRQAPGKEREFVSAISQNSIHTYYADSVKGRFTISRDNSKNTVYLQMNSLRPEDTALYYCAASRFTSWYTADYEYDYWGQGTLVTVSSA |
| 32 | Invention | EVQLVESGGGVVQPGGSLRLSCAASGGTFSTYVMGWFRQAPGKEREFVAAISQNSIHTYYANSVKGRFTISRDNSKNTVYLQLNSLRPEDTALYYCAASRFTSWYTADYEYDYWGQGTLVTVSSA |
| 33 | Invention | EVQLVESGGGVVQPGGSLRLSCAASGGTFSTYVMGWFRQAPGKEREFVAAISQNSIHTYYADSVKGRFTISRDNSKNTVYLQLNSLRPEDTALYYCAASRFTSWYTADYEYDYWGQGTLVTVSSA |
| 34 | Invention | EVQLVESGGGVVQPGGSLRLSCAASGGTFSTYVMGWFRQAPGKEREFVAAISQNSIHTYYANSVKGRFTISRDNSKNTVYLQMNSLRPEDTALYYCAASRFTSWYTADYEYDYWGQGTLVTVSSA |
| 35 | Invention | EVQLVESGGGVVQPGGSLRLSCAASGGTFSTYVMGWFRQAPGKEREFVAAISQNSIHTYYADSVKGRFTISRDNSKNTVYLQMNSLRPEDTALYYCAASRFTSWYTADYEYDYWGQGTLVTVSSA |

Figure 2 (continued)

| SEQ ID NO | Description | Sequence |
|---|---|---|
| 36 | Invention | DVQLVESGGGLVQTGDSLRLSCAASGGTFSTYVMGWFRQAPGKEREFVSAISQNSIHTYYANSVKGRFTISRDNDKNTVYLQLNSLKPEDTAVYYCAASRFTSWYTADYEYDYWGQGTLVTVSS |
| 37 | Invention | DVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSS |
| 38 | Invention | DVQLVESGGGVVQPGGSLRLSCAASGGTFSTYVMGWFRQAPGKEREFVSAISQNSIHTYYADSVKGRFTISRDNSKNTVYLQLNSLRPEDTALYYCAASRFTSWYTADYEYDYWGQGTLVTVSS |
| 39 | Invention | DVQLVESGGGVVQPGGSLRLSCAASGGTFSTYVMGWFRQAPGKEREFVSAISQNSIHTYYANSVKGRFTISRDNSKNTVYLQMNSLRPEDTALYYCAASRFTSWYTADYEYDYWGQGTLVTVSS |
| 40 | Invention | DVQLVESGGGVVQPGGSLRLSCAASGGTFSTYVMGWFRQAPGKEREFVSAISQNSIHTYYADSVKGRFTISRDNSKNTVYLQMNSLRPEDTALYYCAASRFTSWYTADYEYDYWGQGTLVTVSS |
| 41 | Invention | DVQLVESGGGVVQPGGSLRLSCAASGGTFSTYVMGWFRQAPGKEREFVAAISQNSIHTYYANSVKGRFTISRDNSKNTVYLQLNSLRPEDTALYYCAASRFTSWYTADYEYDYWGQGTLVTVSS |
| 42 | Invention | DVQLVESGGGVVQPGGSLRLSCAASGGTFSTYVMGWFRQAPGKEREFVAAISQNSIHTYYADSVKGRFTISRDNSKNTVYLQLNSLRPEDTALYYCAASRFTSWYTADYEYDYWGQGTLVTVSS |
| 43 | Invention | DVQLVESGGGVVQPGGSLRLSCAASGGTFSTYVMGWFRQAPGKEREFVAAISQNSIHTYYANSVKGRFTISRDNSKNTVYLQMNSLRPEDTALYYCAASRFTSWYTADYEYDYWGQGTLVTVSS |
| 44 | Invention | DVQLVESGGGVVQPGGSLRLSCAASGGTFSTYVMGWFRQAPGKEREFVAAISQNSIHTYYADSVKGRFTISRDNSKNTVYLQMNSLRPEDTALYYCAASRFTSWYTADYEYDYWGQGTLVTVSS |

Figure 2 (continued)

| SEQ ID NO | Description | Sequence |
|---|---|---|
| 45 | anti-HER2-Nanobody | EVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSS |
| 46 | Compound of the invention | DVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSGGGGSGGGGSEVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSA |
| 47 | Compound of the invention | DVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSEVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSA |
| 48 | Compound of the invention | DVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSA |
| 49 | Compound of the invention | DVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSGGGGSGGGGSGGGGSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSA |

Figure 2 (continued)

| SEQ ID NO | Description | Sequence |
|---|---|---|
| 50 | Compound of the invention | DVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSGGGGSEVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSA |
| 51 | Compound of the invention | DVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSGGGGSEVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSGGGGSGGGGSGGGGSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSA |
| 52 | Compound of the invention | DVQLVESGGGVVQPGDSLRLSCAASGGTFSTYVMGWFRQAPGKEREFVSAISQNSIHTYYANSVKGRFTISRDNSKNTVYLQLNSLRPEDTALYYCAASRFTSWYTADYEYDYWGQGTLVTVSSGGGGSGGGGSGGGGSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSGGGGSGGGGSGGGGSGGGGSGGGGSGGGGSEVQLVESGGGLVQAGGSLRLSCAASGITFSINTMGWYRQAPGKQRELVALISSIGDTYYADSVKGRFTISRDNAKNTVYLQMNSLKPEDTAVYYCKRFRTAAQGTDYWGQGTLVTVSSA |

Figure 2 (continued)

| SEQ ID NO | Description | Sequence |
|---|---|---|
| 53 | Compound of the invention | DVQLVESGGGVVQPGGSLRLSCAASGRTFSSYAMGWFRQAPGKEREFVAAISWSDGSTYYADSVKGRFTISRDNAKNTVYLQMNSLRPEDTALYYCAADLTSTNPGSYIYIWAYDYWGQGTLVTVSSGGGGSGGGGSGGGGSGGGGSGGGGSGGGGSEVQLVESGGGVVQPGGSLRLSCAASGRTFSSYAMGWFRQAPGKEREFVAAISWSDGSTYYADSVKGRFTISRDNAKNTVYLQMNSLRPEDTALYYCAADLTSTNPGSYIYIWAYDYWGQGTLVTVSSGGGGSGGGGSGGGGSGGGGSGGGGSGGGGSEVQLVESGGGVVQPGGSLRLSCAASGGTFSTYVMGWFRQAPGKEREFVSAISQNSIHTYYANSVKGRFTISRDNSKNTVYLQMNSLRPEDTALYYCAASRFTSWYTADYEYDYWGQGTLVTVSS |

Figure 3A

```
   1 EVQLVESGGG LVQPGNSLRL SCAASGFTFS SFGMSWVRQA PGKGLEWVSS ISGSGSDTLY ADSVKGRFTI SRDNAKTTLY LQMNSLRPED TAVYYCTIGG SLSRSS----       ---QGTLV TVSS 115
   2 .........L ..........G ..........R ..........       ..........      ..........       ..........       ...S.N....       ..........      ..........L.K.. ..........       .......... ....      .... 115
  18 .......... ..........       ....T.D... .G........ TYV.G.F... ER.F..A... QNSIH.Y...  .N........ .D.N.V.... ......L...       ..AASR FT.WYTADYE YDYWG..... 124
  19 .........V ....V.D... .G........ TYV.G.F... ER.F..A...       QNSIH.Y... .N........ .S.N.V....     ......L...       ..AASR FT.WYTADYE YDYWG..... 124
```

Figure 3B

```
  18 EVQLVESGGG LVQTGDSLRL SCAASGGTFS TYVMGWFRQA PGKEREFVSA ISQNSIHTYY ANSVKGRFTI SRDNDKNTVY LQLNSLKPED TAVYYCAASR FTSWYTADYE YDWGQGTLV TVSS 124
  19 .........V ....V..P.N ..........       SFG.S.V...       GL.W..S... .GSGSD.L.. .D........       .......S.. .A.T.L.... ......R... TIGG SL.RSS----       .......... 115
   1 .......... ....L..P.G ..........       F..R SFG.S.V... GP.W..S... .GSGSD.L..       .D........ .......S.. ...L...... ......R... TIGG SL.RSS----       .......... 115
   2 .........L .........L       ..........     ..........     ..........       ..........       ..........       ......M... ..........       .......... .......... 115
```

Figure 5

```
Mouse   MKWVTFLLLLLFVSGSAFSR---GVFRREA---HKSEIAHRYNDLGEQHFKGLVLIAFSQY 54
Rat     MKWVTFLLLLLFISGSAFSR---GVFRREA---HKSEIAHRFKDLGEQHFKGLVLIAFSQY 54
Dog     MKWVTFISLFFLFSSAYSR---GLVRREA---YKSEIAHRYNDLGEEHFRGLVLVAFSQY 54
Cat     MKWVTFISLLLLFSSAYSR---GVTRREA---HQSEIAHRFNDLGEEHFRGLVLVAFSQY 54
Human   MKWVTFISLLFLFSSAYSR---GVFRRDA---HKSEVAHRFKDLGEENFKALVLIAFAQY 54
Cow     MKWVTFISLLLLFSSAYSR---GVFRRDT---HKSEIAHRFKDLGEEHFKGLVLIAFSQY 54
Sheep   MKWVTFISLLLLFSSAYSR---GVFRRDT---HKSEIAHRFNDLGEENFQGLVLIAFSQY 54
Pig     MKWVTFISLLFLFSSAYSR---GVFRRDT---YKSEIAHRFKDLGEQYFKGLVLIAFSQH 54
Horse   MKWVTFVSLLFLFSSAYSR---GVLRRDT---HKSEIAHRFNDLGEKHFKGLVLVAFSQY 54
Rabbit  MKWVTFISLLFLFSSAYSR---GVFRREA---HKSEIAHRFNDVGEEHFIGLVLITFSQY 54

Mouse   LQKCSYDEHAKLVQEVTDFAKTCVADESAANCDKSLHTLFGDKLCAIPNLRENYGELADC 114
Rat     LQKCPYEEHIKLVQEVTDFAKTCVADENAENCDKSIHTLFGDKLCAIPKLRDNYGELADC 114
Dog     LQQCPFEDHVKLAKEVTEFAKACAAEESGANCDKSLHTLFGDKLCTVASLRDKYGMADC 114
Cat     LQQCPFEDHVKLVNEVTEFAKGCVADQSAANCEKSLHELLGDKLCTVASLRDKYGEMADC 114
Human   LQQCPFEDHVKLVNEVTEFAKTCVADESAENCDKSLHTLFGDKLCTVATLRETYGEMADC 114
Cow     LQQCPFDEHVKLVNELTEFAKTCVADESHAGCEKSLHTLFGDELCKVASLRETYGDMADC 114
Sheep   LQQCPFDEHVKLVKELTEFAKTCVADESHAGCDKSLHTLFGDELCKVATLRETYGDMADC 114
Pig     LQQCPYEEHVKLVREVTEFAKTCVADESAENCDKSIHTLFGDKLCAIPSLREHYGDLADC 114
Horse   LQQCPFEDHVKLVNEVTEFAKKCAADESAENCDKSLHTLFGDKLCTVATLRATYGELADC 114
Rabbit  LQKCPYEEHAKLVKEVTDLAKACVADESAANCDKSLHDIFGDKICALPSLRDTYGDVADC 114

Mouse   CTKQEPERNECFLQHKDDNPSLP-PFERPEAEAMCTSFKENPTTFMGHYLHEVARRHPYF 173
Rat     CAKQEPERNECFLQHKDDNPNLP-PFQRPEAEAMCTSFQENPTSFLGHYLHEVARRHPYF 173
Dog     CEKQEPDRNECFLAHKDDNPGFP-PLVAPEPDALCAAFQDNEQLFLGKYLYEIARRHPYF 173
Cat     CEKKEPERNECFLQHKDDNPGFG-QLVTPEADAMCTAFHENEQRFLGKYLYEIARRHPYF 173
Human   CAKQEPERNECFLQHKDDNPNLP-RLVRPEVDVMCTAFHDNEETFLKKYLYEIARRHPYF 173
Cow     CEKQEPERNECFLSHKDDSPDLP-KLK-PDPNTLCDEFKADEKKFWGKYLYEIARRHPYF 172
Sheep   CEKQEPERNECFLNHKDDSPDLP-KLK-PEPDTLCAEFKADEKKFWGKYLYEVARRHPYF 172
Pig     CEKEEPERNECFLQHKNDNPDIP-KLK-PDPVALCADFQEDEQKFWGKYLYEIARRHPYF 172
Horse   CEKQEPERNECFLTHKDDHPNLP-KLK-PEPDAQCAAFQEDPDKFLGKYLYEVARRHPYF 172
Rabbit  CEKKEPERNECFLHHKDDKPDLP-PFARPEADVLCKAFHDDEKAFFGHYLYEVARRHPYF 173

Mouse   YAPELLYYAEQYNEILTQCCAEADKESCLTPKLDGVKEKALVSSVRQRMKCSSMQKFGER 233
Rat     YAPELLYYAEKYNEVLTQCCTESDKAACLTPKLDAVKEKALVAAVRQRMKCSSMQRFGER 233
Dog     YAPELLYYAQQYKGVFAECCQAADKAACLGPKIEALREKVLLSSAKERFKCASLQKFGDR 233
Cat     YAPELLYYAEEYKGVFTECCEAADKAACLTPKVDALREKVLASSAKERLKCASLQKFGER 233
Human   YAPELLFFAKRYKAAPFTECCQAADKAACLLPKLDELRDEGKASSAKQRLKCASLQKFGER 233
Cow     YAPELLYYANKYNGVFQECCQAEDKGACLLPKIETMREKVLTSSARQRLRCASIQKFGER 232
Sheep   YAPELLYYANKYNGVFQECCQAEDKGACLLPKIDAMREKVLASSARQRLRCASIQKFGER 232
Pig     YAPELLYYAIIYKDVFSECCQAADKAACLLPKIEHLREKVLTSAAKQRLKCASIQKFGER 232
Horse   YGPELLFHAEEYKADFTECCPADDKLACLIPKLDALKERILLSSAKERLKCSSFQNFGER 232
Rabbit  YAPELLYYAQKYKAILTECCEAADKGACLTPKLDALEGKSLISAAQERLRCASIQKFGDR 233

Mouse   AFKAWAVARLSQTFPNADFAEITKLATDLTKVNKECCHGDLLECADDRAELAKYMCENQA 293
Rat     AFKAWAVARMSQRFPNAEFAEITKLATDLTKINKECCHGDLLECADDRAELAKYMCENQA 293
Dog     AFKAWSVARLSQRFPKADFAEISKVVTDLTKVHKECCHGDLLECADDRADLAKYMCENQD 293
Cat     AFKAWSVARLSQKFPKAEFAEISKLVTDLAKIHKECCHGDLLECADDRADLAKYICENQD 293
Human   AFKAWAVARLSQRFPKAEFAEVSKLVTDLTKVHTECCHGDLLECADDRADLAKYICENQD 293
Cow     ALKAWSVARLSQKFPKAEFVEVTKLVTDLTKVHKECCHGDLLECADDRADLAKYICDNQD 292
Sheep   ALKAWSVARLSQKFPKADFTDVTKIVTDLTKVHKECCHGDLLECADDRADLAKYICDHQD 292
Pig     AFKAWSLARLSQRFPKADFTEISKIVTDLAKVHKECCHGDLLECADDRADLAKYICENQD 292
Horse   AVKAWSVARLSQKFPKADFAEVSKIVTDLTKVHKECCHGDLLECADDRADLAKYICEHQD 292
Rabbit  AYKAWALVRLSQRFPKADFTDISKIVTDLTKVHKECCHGDLLECADDRADLAKYMCEHQE 293
```

Figure 5 (continued)

```
Mouse    TISSKLQTCCDKPLLKKAHCLSEVEHDTMPADLPAIAADFVEDQEVCKNYAEAKDVFLGT 353
Rat      TISSKLQACCDKPVLQKSQCLAEIEHDNIPADLPSIAADFVEDKEVCKNYAEAKDVFLGT 353
Dog      SISTKLKECCDKPVLEKSQCLAEVERDELPGDLPSLAADFVEDKEVCKNYQEAKDVFLGT 353
Cat      SISTKLKECCGKPVLEKSHCISEVERDELPADLPPLAVDFVEDKEVCKNYQEAKDVFLGT 353
Human    SISSKLKECCEKPLLEKSHCIAEVENDEMPADLPSLAADFVESKDVCKNYAEAKDVFLGM 353
Cow      TISSKLKECCDKPLLEKSHCIAEVEKDAIPENLPPLTADFAEDKDVCKNYQEAKDAFLGS 352
Sheep    ALSSKLKECCDKPVLEKSHCIAEVDKDAVPENLPPLTADFAEDKEVCKNYQEAKDVFLGS 352
Pig      TISTKLKECCDKPLLEKSHCIAEAKRDELPADLNPLEHDFVEDKEVCKNYKEAKHVFLGT 352
Horse    SISGKLKACCDKPLLQKSHCIAEVKEDDLPSDLPALAADFAEDKEICKHYKDAKDVFLGT 352
Rabbit   TISSHLKECCDKPILEKAHCIYGLHNDETPAGLPAVAEEFVEDKDVCKNYEEAKDLFLGK 353

Mouse    FLYEYSRRHPDYSVSLLLRLAKKYEATLEKCCAEANPPACYGTVLAEFQPLVEEPKNLVK 413
Rat      FLYEYSRRHPDYSVSLLLRLAKKYEATLEKCCAEGDPPACYGTVLAEFQPLVEEPKNLVK 413
Dog      FLYEYARRHPEYSVSLLLRLAKEYEATLEKCCATDDPPTCYAKVLDEFKPLVDEPQNLVK 413
Cat      FLYEYSRRHPEYSVSLLLRLAKEYEATLEKCCATDDPPACYAHVFDEFKPLVEEPHNLVK 413
Human    FLYEYARRHPDYSVVLLLRLAKTYETTLEKCCAAADPHECYAKVFDEFKPLVEEPQNLIK 413
Cow      FLYEYSRRHPEYAVSVLLRLAKEYEATLEECCAKDDPHACYSTVFDKLKHLVDEPQNLIK 412
Sheep    FLYEYSRRHPEYAVSVLLRLAKEYEATLEDCCAKEDPHACYATVFDKLKHLVDEPQNLIK 412
Pig      FLYEYSRRHPDYSVSLLLRIAKIYEATLEDCCAKEDPPACYATVFDKFQPLVDEPKNLIK 412
Horse    FLYEYSRRHPDYSVSLLLRIAKTYEATLEKCCAEADPPACYRTVFDQFTPLVEEPKSLVK 412
Rabbit   FLYEYSRRHPDYSVVLLLRLGKAYEATLKKCCATDDPHACYAKVLDEFQPLVDEPKNLVK 413

Mouse    TNCDLYEKLGEYGFQNAILVRYTQKAPQVSTPTLVEAARNLGRVGTKCCTLPEDQRLPCV 473
Rat      TNCELYEKLGEYGFQNAILVRYTQKAPQVSTPTLVEAARNLGRVGTKCCTLPEAQRLPCV 473
Dog      TNCELFEKLGEYGFQNALLVRYTKKAPQVSTPTLVEVSRKLGKVGTKCCKKPESERMSCA 473
Cat      TNCELFEKLGEYGFQNALLVRYTKKVPQVSTPTLVEVSRSLGKVGSKCCTHPEAERLSCA 473
Human    QNCELFEQLGEYKFQNALLVRYTKKVPQVSTPTLVEVSRNLGKVGSKCCKHPEAKRMPCA 473
Cow      QNCDQFEKLGEYGFQNALIVRYTRKVPQVSTPTLVEVSRSLGKVGTRCCTKPESERMPCT 472
Sheep    KNCELFEKHGEYGFQNALIVRYTRKAPQVSTPTLVEISRSLGKVGTKCCAKPESERMPCT 472
Pig      QNCELFEKLGEYGFQNALIVRYTKKVPQVSTPTLVEVARKLGLVGSRCCKRPEEERLSCA 472
Horse    KNCDLFEEVGEYDFQNALIVRYTKKAPQVSTPTLVEIGRTLGKVGSRCCKLPESERLPCS 472
Rabbit   QNCELYEQLGDYNFQNALLVRYTKKVPQVSTPTLVEISRSLGKVGSKCCKHPEAERLPCV 473

Mouse    EDYLSAILNRVCLLHEKTPVSEHVTKCCSGSLVERRPCFSALTVDETYVPKEFKAETFTF 533
Rat      EDYLSAILNRLCVLHEKTPVSEKVTKCCSGSLVERRPCFSALTVDETYVPKEFKAETFTF 533
Dog      EDFLSVVLNRLCVLHEKTPVSERVTKCCSESLVNRRPCFSGLEVDETYVPKEFNAETFTF 533
Cat      EDYLSVVLNRLCVLHEKTPVSERVTKCCTESLVNRRPCFSALQVDETYVPKEFSAETFTF 533
Human    EDYLSVVLNQLCVLHEKTPVSDRVTKCCTESLVNRRPCFSALEVDETYVPKEFNAETFTF 533
Cow      EDYLSLILNRLCVLHEKTPVSEKVTKCCTESLVNRRPCFSALTPDETYVPKAFDEKLFTF 532
Sheep    EDYLSLILNRLCVLHEKTPVSEKVTKCCTESLVNRRPCFSDLTLDETYVPKPFDEKFFTF 532
Pig      EDYLSLVLNRLCVLHEKTPVSEKVTKCCTESLVNRRPCFSALTPDETYKPKEFVEGTFTF 532
Horse    ENHLALALNRLCVLHEKTPVSEKITKCCTDSLAERRPCFSALELDEGYVPKEFKAETFTF 532
Rabbit   EDYLSVVLNRLCVLHEKTPVSEKVTKCCSESLVDRRPCFSALGPDETYVPKEFNAETFTF 533

Mouse    HSDICTLPEKEKQIKKQTALAELVKHKPKATAEQLKTVMDDFAQFLDTCCKAADKDTCFS 593
Rat      HSDICTLPDKEKQIKKQTALAELVKHKPKATEDQLKTVMGDFAQFVDKCCKAADKDNCFA 593
Dog      HADLCTLPEAEKQVKKQTALVELLKHKPKATDEQLKTVMGDFGAFVEKCCAAENKEGCFS 593
Cat      HADLCTLPEAEKQIKKQSALVELLKHKPKATEEQLKTVMGDFGSFVDKCCAAEDKEACFA 593
Human    HADICTLSEKERQIKKQTALVELVKHKPKATKEQLKAVMDDFAAFVEKCCKADDKETCFA 593
Cow      HADICTLPDTEKQIKKQTALVELLKHKPKATEEQLKTVMENFVAFVDKCCAADDKEACFA 592
Sheep    HADICTLPDTEKQIKKQTALVELLKHKPKATDEQLKTVMENFVAFVDKCCAADDKEGCFV 592
Pig      HADLCTLPEDEKQIKKQTALVELLKHKPHATEEQLRTVLGNFAAFVQKCCAAPDHEACFA 592
Horse    HADICTLPEDEKQIKKQSALAELVKHKPKATKEQLKTVLGNFSAFVAKCCGREDKEACFA 592
Rabbit   HADICTLPETERKIKKQTALVELVKHKPHATNDQLKTVVGEFTALLDKCCSAEDKEACFA 593
```

Figure 5 (continued)

```
Mouse    TEGPNLVTRCKDTLA---  608
Rat      TEGPNLVARSKEALA---  608
Dog      EEGPKLVAAAQAALV---  608
Cat      EEGPKLVAAAQAALA---  608
Human    EEGKKLVAASQAALGL--  609
Cow      VEGPKLVVSTQTALA---  607
Sheep    LEGPKLVASTQAALA---  607
Pig      VEGPKFVIEIRGILA---  607
Horse    EEGPKLVASSQLALA---  607
Rabbit   VEGPKLVESSKATLG---  608
```

▲ = His6Flag3-SEQ ID NO:1
■ = Flag3His6- SEQ ID NO:19
● = cAblys3-Flag3His6 ()

SEQUENCE LISTING

```
<160> NUMBER OF SEQ ID NOS: 63

<210> SEQ ID NO 1
<211> LENGTH: 115
<212> TYPE: PRT
<213> ORGANISM: Artificial Sequence
<220> FEATURE:
<223> OTHER INFORMATION: Reference

<400> SEQUENCE: 1

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Reference

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 3
<211> LENGTH: 5
<212> TYPE: PRT
<213> ORGANISM: Artificial Sequence
<220> FEATURE:
<223> OTHER INFORMATION: CDR1 (Kabat)

<400> SEQUENCE: 3

Ser Phe Gly Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: CDR2 (Kabat)

<400> SEQUENCE: 4

Ser Ile Ser Gly Ser Gly Ser Asp Thr Leu Tyr Ala Asp Ser Val Lys
1               5                   10                  15

Gly

<210> SEQ ID NO 5
<211> LENGTH: 6
<212> TYPE: PRT
<213> ORGANISM: Artificial Sequence
<220> FEATURE:
<223> OTHER INFORMATION: CDR3 (Kabat/Abm)

<400> SEQUENCE: 5

Gly Gly Ser Leu Ser Arg
1               5

<210> SEQ ID NO 6
<211> LENGTH: 10
<212> TYPE: PRT
<213> ORGANISM: Artificial Sequence
<220> FEATURE:
<223> OTHER INFORMATION: CDR1 (Abm)

<400> SEQUENCE: 6

Gly Phe Thr Phe Arg Ser Phe Gly Met Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: CDR2 (Abm)

<400> SEQUENCE: 7

Ser Ile Ser Gly Ser Gly Ser Asp Thr Leu
```

```
<210> SEQ ID NO 8
<211> LENGTH: 6
<212> TYPE: PRT
<213> ORGANISM: Artificial Sequence
<220> FEATURE:
<223> OTHER INFORMATION: CDR3 (Kabat/Abm)

<400> SEQUENCE: 8

Gly Gly Ser Leu Ser Arg
1               5

<210> SEQ ID NO 9
<211> LENGTH: 5
<212> TYPE: PRT
<213> ORGANISM: Artificial Sequence
<220> FEATURE:
<223> OTHER INFORMATION: CDR1 (Kabat)

<400> SEQUENCE: 9

Thr Tyr Val Met Gly
1               5

<210> SEQ ID NO 10
<211> LENGTH: 17
<212> TYPE: PRT
<213> ORGANISM: Artificial Sequence
<220> FEATURE:
<223> OTHER INFORMATION: CDR2 (Kabat)

<400> SEQUENCE: 10

Ala Ile Ser Gln Asn Ser Ile His Thr Tyr Tyr Ala Asn Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: CDR2 (Kabat)

<400> SEQUENCE: 11

Ala Ile Ser Gln Asn Ser Ile His Thr Tyr Tyr Ala Asp Ser Val Lys
1               5                   10                  15

Gly

<210> SEQ ID NO 12
<211> LENGTH: 10
<212> TYPE: PRT
<213> ORGANISM: Artificial Sequence
<220> FEATURE:
<223> OTHER INFORMATION: CDR1 (Abm)

<400> SEQUENCE: 12

Gly Gly Thr Phe Ser Thr Tyr Val Met Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDR2 (Abm)
```

```
<400> SEQUENCE: 13

Ala Ile Ser Gln Asn Ser Ile His Thr Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: CDR3 (Kabat/Abm)

<400> SEQUENCE: 14

Ser Arg Phe Thr Ser Trp Tyr Thr Ala Asp Tyr Glu Tyr Asp Tyr
1               5                   10                  15

<210> SEQ ID NO 15
<211> LENGTH: 5
<212> TYPE: PRT
<213> ORGANISM: Artificial Sequence
<220> FEATURE:
<223> OTHER INFORMATION: C-terminal sequence

<400> SEQUENCE: 15

Val Thr Val Ser Ser
1               5

<210> SEQ ID NO 16
<211> LENGTH: 15
<212> TYPE: PRT
<213> ORGANISM: Artificial Sequence
<220> FEATURE:
<223> OTHER INFORMATION: 15 GS linker

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 35
<212> TYPE: PRT
<213> ORGANISM: Artificial Sequence
<220> FEATURE:
<223> OTHER INFORMATION: 35 GS linker

<400> SEQUENCE: 17

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 18
<211> LENGTH: 124
<212> TYPE: PRT
<213> ORGANISM: Artificial Sequence
<220> FEATURE:
<223> OTHER INFORMATION: ISVD

<400> SEQUENCE: 18

Glu Val Gln Leu Val Glu Ser Gly Gly Gly Leu Val Gln Thr Gly Asp
1               5                   10                  15

Ser Leu Arg Leu Ser Cys Ala Ala Ser Gly Gly Thr Phe Ser Thr Tyr
            20                  25                  30
```

```
Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Asp Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 19
<211> LENGTH: 124
<212> TYPE: PRT
<213> ORGANISM: Artificial Sequence
<220> FEATURE:
<223> OTHER INFORMATION: ISVD

<400> SEQUENCE: 19

Glu Val Gln Leu Val Glu Ser Gly Gly Gly Val Val Gln Pro Gly Asp
1               5                   10                  15

Ser Leu Arg Leu Ser Cys Ala Ala Ser Gly Gly Thr Phe Ser Thr Tyr
                20                  25                  30

Val Met Gly Trp Phe Arg Gln Ala Pro Gly Lys Glu Arg Glu Phe Val
            35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 20
<211> LENGTH: 124
<212> TYPE: PRT
<213> ORGANISM: Artificial Sequence
<220> FEATURE:
<223> OTHER INFORMATION: ISVD

<400> SEQUENCE: 20

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
                20                  25                  30

Val Met Gly Trp Phe Arg Gln Ala Pro Gly Lys Glu Arg Glu Phe Val
            35                  40                  45

Ser Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95
```

```
Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 21
<211> LENGTH: 124
<212> TYPE: PRT
<213> ORGANISM: Artificial Sequence
<220> FEATURE:
<223> OTHER INFORMATION: ISVD

<400> SEQUENCE: 21

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 22
<211> LENGTH: 124
<212> TYPE: PRT
<213> ORGANISM: Artificial Sequence
<220> FEATURE:
<223> OTHER INFORMATION: ISVD

<400> SEQUENCE: 22

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 23
<211> LENGTH: 124
<212> TYPE: PRT
```

<213> ORGANISM: Artificial Sequence
<220> FEATURE:
<223> OTHER INFORMATION: ISVD

<400> SEQUENCE: 23

```
Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120
```

<210> SEQ ID NO 24
<211> LENGTH: 124
<212> TYPE: PRT
<213> ORGANISM: Artificial Sequence
<220> FEATURE:
<223> OTHER INFORMATION: ISVD

<400> SEQUENCE: 24

```
Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120
```

<210> SEQ ID NO 25
<211> LENGTH: 124
<212> TYPE: PRT
<213> ORGANISM: Artificial Sequence
<220> FEATURE:
<223> OTHER INFORMATION: ISVD

<400> SEQUENCE: 25

```
Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30
```

Val Met Gly Trp Phe Arg Gln Ala Pro Gly Lys Glu Arg Glu Phe Val
            35                  40                  45

Ala Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
                100                 105                 110

Tyr Trp Gly Gln Gly Thr Leu Val Thr Val Ser Ser
                115                 120

<210> SEQ ID NO 26
<211> LENGTH: 124
<212> TYPE: PRT
<213> ORGANISM: Artificial Sequence
<220> FEATURE:
<223> OTHER INFORMATION: ISVD

<400> SEQUENCE: 26

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
            35                  40                  45

Ala Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
                100                 105                 110

Tyr Trp Gly Gln Gly Thr Leu Val Thr Val Ser Ser
                115                 120

<210> SEQ ID NO 27
<211> LENGTH: 125
<212> TYPE: PRT
<213> ORGANISM: Artificial Sequence
<220> FEATURE:
<223> OTHER INFORMATION: ISVD

<400> SEQUENCE: 27

Glu Val Gln Leu Val Glu Ser Gly Gly Gly Leu Val Gln Thr Gly Asp
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
            35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Asp Lys Asn Thr Val Tyr
65                  70                  75                  80

Leu Gln Leu Asn Ser Leu Lys Pro Glu Asp Thr Ala Val Tyr Tyr Cys

```
                  85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
            115                 120                 125

<210> SEQ ID NO 28
<211> LENGTH: 125
<212> TYPE: PRT
<213> ORGANISM: Artificial Sequence
<220> FEATURE:
<223> OTHER INFORMATION: ISVD

<400> SEQUENCE: 28

Glu Val Gln Leu Val Glu Ser Gly Gly Gly Val Val Gln Pro Gly Asp
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
            115                 120                 125

<210> SEQ ID NO 29
<211> LENGTH: 125
<212> TYPE: PRT
<213> ORGANISM: Artificial Sequence
<220> FEATURE:
<223> OTHER INFORMATION: ISVD

<400> SEQUENCE: 29

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
            115                 120                 125

<210> SEQ ID NO 30
<211> LENGTH: 125
```

```
<212> TYPE: PRT
<213> ORGANISM: Artificial Sequence
<220> FEATURE:
<223> OTHER INFORMATION: ISVD

<400> SEQUENCE: 30

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
        115                 120                 125

<210> SEQ ID NO 31
<211> LENGTH: 125
<212> TYPE: PRT
<213> ORGANISM: Artificial Sequence
<220> FEATURE:
<223> OTHER INFORMATION: ISVD

<400> SEQUENCE: 31

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
        115                 120                 125

<210> SEQ ID NO 32
<211> LENGTH: 125
<212> TYPE: PRT
<213> ORGANISM: Artificial Sequence
<220> FEATURE:
<223> OTHER INFORMATION: ISVD

<400> SEQUENCE: 32

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
```

```
                20                  25                  30
Val Met Gly Trp Phe Arg Gln Ala Pro Gly Lys Glu Arg Glu Phe Val
            35                  40                  45

Ala Ala Ile Ser Gln Asn Ser Ile His Thr Tyr Tyr Ala Asn Ser Val
        50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
        115                 120                 125

<210> SEQ ID NO 33
<211> LENGTH: 125
<212> TYPE: PRT
<213> ORGANISM: Artificial Sequence
<220> FEATURE:
<223> OTHER INFORMATION: ISVD

<400> SEQUENCE: 33

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
            35                  40                  45

Ala Ala Ile Ser Gln Asn Ser Ile His Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
        115                 120                 125

<210> SEQ ID NO 34
<211> LENGTH: 125
<212> TYPE: PRT
<213> ORGANISM: Artificial Sequence
<220> FEATURE:
<223> OTHER INFORMATION: ISVD

<400> SEQUENCE: 34

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
            35                  40                  45

Ala Ala Ile Ser Gln Asn Ser Ile His Thr Tyr Tyr Ala Asn Ser Val
        50                  55                  60

Lys Gly Arg Phe Thr Ile Ser Arg Asp Asn Ser Lys Asn Thr Val Tyr
65                  70                  75                  80
```

```
Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
        115                 120                 125

<210> SEQ ID NO 35
<211> LENGTH: 125
<212> TYPE: PRT
<213> ORGANISM: Artificial Sequence
<220> FEATURE:
<223> OTHER INFORMATION: ISVD

<400> SEQUENCE: 35

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Ala
        115                 120                 125

<210> SEQ ID NO 36
<211> LENGTH: 124
<212> TYPE: PRT
<213> ORGANISM: Artificial Sequence
<220> FEATURE:
<223> OTHER INFORMATION: ISVD

<400> SEQUENCE: 36

Asp Val Gln Leu Val Glu Ser Gly Gly Gly Leu Val Gln Thr Gly Asp
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Asp Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 37
```

```
<211> LENGTH: 124
<212> TYPE: PRT
<213> ORGANISM: Artificial Sequence
<220> FEATURE:
<223> OTHER INFORMATION: ISVD

<400> SEQUENCE: 37

Asp Val Gln Leu Val Glu Ser Gly Gly Gly Val Val Gln Pro Gly Asp
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 38
<211> LENGTH: 124
<212> TYPE: PRT
<213> ORGANISM: Artificial Sequence
<220> FEATURE:
<223> OTHER INFORMATION: ISVD

<400> SEQUENCE: 38

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 39
<211> LENGTH: 124
<212> TYPE: PRT
<213> ORGANISM: Artificial Sequence
<220> FEATURE:
<223> OTHER INFORMATION: ISVD

<400> SEQUENCE: 39

Asp Val Gln Leu Val Glu Ser Gly Gly Gly Val Val Gln Pro Gly Gly
1               5                   10                  15
```

```
Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120
```

<210> SEQ ID NO 40
<211> LENGTH: 124
<212> TYPE: PRT
<213> ORGANISM: Artificial Sequence
<220> FEATURE:
<223> OTHER INFORMATION: ISVD

<400> SEQUENCE: 40

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120
```

<210> SEQ ID NO 41
<211> LENGTH: 124
<212> TYPE: PRT
<213> ORGANISM: Artificial Sequence
<220> FEATURE:
<223> OTHER INFORMATION: ISVD

<400> SEQUENCE: 41

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80
```

```
Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 42
<211> LENGTH: 124
<212> TYPE: PRT
<213> ORGANISM: Artificial Sequence
<220> FEATURE:
<223> OTHER INFORMATION: ISVD

<400> SEQUENCE: 42

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 43
<211> LENGTH: 124
<212> TYPE: PRT
<213> ORGANISM: Artificial Sequence
<220> FEATURE:
<223> OTHER INFORMATION: ISVD

<400> SEQUENCE: 43

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120
```

```
<210> SEQ ID NO 44
<211> LENGTH: 124
<212> TYPE: PRT
<213> ORGANISM: Artificial Sequence
<220> FEATURE:
<223> OTHER INFORMATION: ISVD

<400> SEQUENCE: 44

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Gln Asn Ser Ile His Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser
        115                 120

<210> SEQ ID NO 45
<211> LENGTH: 118
<212> TYPE: PRT
<213> ORGANISM: Artificial Sequence
<220> FEATURE:
<223> OTHER INFORMATION: anti-HER2-Nanobody

<400> SEQUENCE: 45

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser
        115

<210> SEQ ID NO 46
<211> LENGTH: 278
<212> TYPE: PRT
<213> ORGANISM: Artificial Sequence
<220> FEATURE:
<223> OTHER INFORMATION: bivalent bispecific compound

<400> SEQUENCE: 46

Asp Val Gln Leu Val Glu Ser Gly Gly Gly Leu Val Gln Ala Gly Gly
1               5                   10                  15
```

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Gly Gly Gly Ser Gly Gly Gly Gly Ser Gly
130                 135                 140

Gly Gly Gly Ser Gly Gly Gly Ser Glu Val Gln Leu Val Glu Ser
145                 150                 155                 160

Gly Gly Gly Val Val Gln Pro Gly Asp Ser Leu Arg Leu Ser Cys Ala
            165                 170                 175

Ala Ser Gly Gly Thr Phe Ser Thr Tyr Val Met Gly Trp Phe Arg Gln
            180                 185                 190

Ala Pro Gly Lys Glu Arg Glu Phe Val Ser Ala Ile Ser Gln Asn Ser
            195                 200                 205

Ile His Thr Tyr Tyr Ala Asn Ser Val Lys Gly Arg Phe Thr Ile Ser
            210                 215                 220

Arg Asp Asn Ser Lys Asn Thr Val Tyr Leu Gln Leu Asn Ser Leu Arg
225                 230                 235                 240

Pro Glu Asp Thr Ala Leu Tyr Tyr Cys Ala Ala Ser Arg Phe Thr Ser
            245                 250                 255

Trp Tyr Thr Ala Asp Tyr Glu Tyr Asp Tyr Trp Gly Gln Gly Thr Leu
            260                 265                 270

Val Thr Val Ser Ser Ala
            275

<210> SEQ ID NO 47
<211> LENGTH: 258
<212> TYPE: PRT
<213> ORGANISM: Artificial Sequence
<220> FEATURE:
<223> OTHER INFORMATION: bivalent bispecific compound

<400> SEQUENCE: 47

Asp Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
 50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

```
Arg Phe Arg Thr Ala Ala Gln Gly Thr Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Glu Val Gln Leu Val Glu Ser Gly Gly Gly Val
        130                 135                 140

Val Gln Pro Gly Asp Ser Leu Arg Leu Ser Cys Ala Ala Ser Gly Gly
145                 150                 155                 160

Thr Phe Ser Thr Tyr Val Met Gly Trp Phe Arg Gln Ala Pro Gly Lys
                165                 170                 175

Glu Arg Glu Phe Val Ser Ala Ile Ser Gln Asn Ser Ile His Thr Tyr
            180                 185                 190

Tyr Ala Asn Ser Val Lys Gly Arg Phe Thr Ile Ser Arg Asp Asn Ser
        195                 200                 205

Lys Asn Thr Val Tyr Leu Gln Leu Asn Ser Leu Arg Pro Glu Asp Thr
225                 210                 215                 220

Ala Leu Tyr Tyr Cys Ala Ala Ser Arg Phe Thr Ser Trp Tyr Thr Ala
225                 230                 235                 240

Asp Tyr Glu Tyr Asp Tyr Trp Gly Gln Gly Thr Leu Val Thr Val Ser
                245                 250                 255

Ser Ala

<210> SEQ ID NO 48
<211> LENGTH: 258
<212> TYPE: PRT
<213> ORGANISM: Artificial Sequence
<220> FEATURE:
<223> OTHER INFORMATION: bivalent bispecific compound

<400> SEQUENCE: 48

Asp Val Gln Leu Val Glu Ser Gly Gly Gly Val Val Gln Pro Gly Asp
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Glu Val Gln Leu Val
    130                 135                 140

Glu Ser Gly Gly Gly Leu Val Gln Ala Gly Gly Ser Leu Arg Leu Ser
145                 150                 155                 160

Cys Ala Ala Ser Gly Ile Thr Phe Ser Ile Asn Thr Met Gly Trp Tyr
                165                 170                 175

Arg Gln Ala Pro Gly Lys Gln Arg Glu Leu Val Ala Leu Ile Ser Ser
            180                 185                 190
```

Ile Gly Asp Thr Tyr Tyr Ala Asp Ser Val Lys Gly Arg Phe Thr Ile
            195                 200                 205

Ser Arg Asp Asn Ala Lys Asn Thr Val Tyr Leu Gln Met Asn Ser Leu
210                 215                 220

Lys Pro Glu Asp Thr Ala Val Tyr Tyr Cys Lys Arg Phe Arg Thr Ala
225                 230                 235                 240

Ala Gln Gly Thr Asp Tyr Trp Gly Gln Gly Thr Leu Val Thr Val Ser
            245                 250                 255

Ser Ala

<210> SEQ ID NO 49
<211> LENGTH: 278
<212> TYPE: PRT
<213> ORGANISM: Artificial Sequence
<220> FEATURE:
<223> OTHER INFORMATION: bivalent bispecific compound

<400> SEQUENCE: 49

Asp Val Gln Leu Val Glu Ser Gly Gly Gly Val Gln Pro Gly Asp
1               5                   10                  15

Ser Leu Arg Leu Ser Cys Ala Ala Ser Gly Gly Thr Phe Ser Thr Tyr
                20                  25                  30

Val Met Gly Trp Phe Arg Gln Ala Pro Gly Lys Glu Arg Glu Phe Val
            35                  40                  45

Ser Ala Ile Ser Gln Asn Ser Ile His Thr Tyr Tyr Ala Asn Ser Val
        50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Leu Val Gln Ala Gly Gly Ser
                165                 170                 175

Leu Arg Leu Ser Cys Ala Ala Ser Gly Ile Thr Phe Ser Ile Asn Thr
            180                 185                 190

Met Gly Trp Tyr Arg Gln Ala Pro Gly Lys Gln Arg Glu Leu Val Ala
        195                 200                 205

Leu Ile Ser Ser Ile Gly Asp Thr Tyr Tyr Ala Asp Ser Val Lys Gly
    210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Val Tyr Tyr Cys Lys Arg
                245                 250                 255

Phe Arg Thr Ala Ala Gln Gly Thr Asp Tyr Trp Gly Gln Gly Thr Leu
            260                 265                 270

Val Thr Val Ser Ser Ala
        275

-continued

<210> SEQ ID NO 50
<211> LENGTH: 431
<212> TYPE: PRT
<213> ORGANISM: Artificial Sequence
<220> FEATURE:
<223> OTHER INFORMATION: trivalent bispecific compound

<400> SEQUENCE: 50

```
Asp Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Ala Gly Gly Ser Leu Arg Leu Ser Cys Ala
                165                 170                 175

Ala Ser Gly Ile Thr Phe Ser Ile Asn Thr Met Gly Trp Tyr Arg Gln
            180                 185                 190

Ala Pro Gly Lys Gln Arg Glu Leu Val Ala Leu Ile Ser Ser Ile Gly
        195                 200                 205

Asp Thr Tyr Tyr Ala Asp Ser Val Lys Gly Arg Phe Thr Ile Ser Arg
    210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Lys Arg Phe Arg Thr Ala Ala Gln
                245                 250                 255

Gly Thr Asp Tyr Trp Gly Gln Gly Thr Leu Val Thr Val Ser Ser Gly
            260                 265                 270

Gly Gly Gly Ser Gly Gly Gly Gly Ser Gly Gly Gly Ser Gly Gly
        275                 280                 285

Gly Gly Ser Gly Gly Gly Gly Ser Gly Gly Gly Ser Gly Gly Gly
    290                 295                 300

Gly Ser Glu Val Gln Leu Val Glu Ser Gly Gly Gly Val Val Gln Pro
305                 310                 315                 320

Gly Asp Ser Leu Arg Leu Ser Cys Ala Ala Ser Gly Gly Thr Phe Ser
                325                 330                 335

Thr Tyr Val Met Gly Trp Phe Arg Gln Ala Pro Gly Lys Glu Arg Glu
            340                 345                 350

Phe Val Ser Ala Ile Ser Gln Asn Ser Ile His Thr Tyr Tyr Ala Asn
        355                 360                 365

Ser Val Lys Gly Arg Phe Thr Ile Ser Arg Asp Asn Ser Lys Asn Thr
```

```
                370                 375                 380
Val Tyr Leu Gln Leu Asn Ser Leu Arg Pro Glu Asp Thr Ala Leu Tyr
385                 390                 395                 400

Tyr Cys Ala Ala Ser Arg Phe Thr Ser Trp Tyr Thr Ala Asp Tyr Glu
                405                 410                 415

Tyr Asp Tyr Trp Gly Gln Gly Thr Leu Val Thr Val Ser Ser Ala
                420                 425                 430

<210> SEQ ID NO 51
<211> LENGTH: 431
<212> TYPE: PRT
<213> ORGANISM: Artificial Sequence
<220> FEATURE:
<223> OTHER INFORMATION: trivalent bispecific compound

<400> SEQUENCE: 51

Asp Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
                20                  25                  30

Thr Met Gly Trp Tyr Arg Gln Ala Pro Gly Lys Gln Arg Glu Leu Val
            35                  40                  45

Ala Leu Ile Ser Ser Ile Gly Asp Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Gly Gly Gly Ser Gly Gly Gly Ser Gly
        130                 135                 140

Gly Gly Gly Ser Gly Gly Gly Ser Glu Val Gln Leu Val Glu Ser
145                 150                 155                 160

Gly Gly Gly Val Val Gln Pro Gly Asp Ser Leu Arg Leu Ser Cys Ala
                165                 170                 175

Ala Ser Gly Gly Thr Phe Ser Thr Tyr Val Met Gly Trp Phe Arg Gln
                180                 185                 190

Ala Pro Gly Lys Glu Arg Glu Phe Val Ser Ala Ile Ser Gln Asn Ser
            195                 200                 205

Ile His Thr Tyr Tyr Ala Asn Ser Val Lys Gly Arg Phe Thr Ile Ser
        210                 215                 220

Arg Asp Asn Ser Lys Asn Thr Val Tyr Leu Gln Leu Asn Ser Leu Arg
225                 230                 235                 240

Pro Glu Asp Thr Ala Leu Tyr Tyr Cys Ala Ala Ser Arg Phe Thr Ser
                245                 250                 255

Trp Tyr Thr Ala Asp Tyr Glu Tyr Asp Tyr Trp Gly Gln Gly Thr Leu
                260                 265                 270

Val Thr Val Ser Ser Gly Gly Gly Gly Ser Gly Gly Gly Gly Ser Gly
            275                 280                 285

Gly Gly Ser Gly Gly Gly Gly Ser Gly Gly Gly Ser Gly Gly
        290                 295                 300

Gly Gly Ser Gly Gly Gly Gly Ser Glu Val Gln Leu Val Glu Ser Gly
```

```
                    305                 310                 315                 320
Gly Gly Leu Val Gln Ala Gly Gly Ser Leu Arg Leu Ser Cys Ala Ala
                325                 330                 335

Ser Gly Ile Thr Phe Ser Ile Asn Thr Met Gly Trp Tyr Arg Gln Ala
                340                 345                 350

Pro Gly Lys Gln Arg Glu Leu Val Ala Leu Ile Ser Ser Ile Gly Asp
                355                 360                 365

Thr Tyr Tyr Ala Asp Ser Val Lys Gly Arg Phe Thr Ile Ser Arg Asp
            370                 375                 380

Asn Ala Lys Asn Thr Val Tyr Leu Gln Met Asn Ser Leu Lys Pro Glu
385                 390                 395                 400

Asp Thr Ala Val Tyr Tyr Cys Lys Arg Phe Arg Thr Ala Ala Gln Gly
                405                 410                 415

Thr Asp Tyr Trp Gly Gln Gly Thr Leu Val Thr Val Ser Ala
                420                 425                 430

<210> SEQ ID NO 52
<211> LENGTH: 431
<212> TYPE: PRT
<213> ORGANISM: Artificial Sequence
<220> FEATURE:
<223> OTHER INFORMATION: trivalent bispecific compound

<400> SEQUENCE: 52

Asp Val Gln Leu Val Glu Ser Gly Gly Gly Val Val Gln Pro Gly Asp
1               5                   10                  15

Ser Leu Arg Leu Ser Cys Ala Ala Ser Gly Gly Thr Phe Ser Thr Tyr
            20                  25                  30

Val Met Gly Trp Phe Arg Gln Ala Pro Gly Lys Glu Arg Glu Phe Val
        35                  40                  45

Ser Ala Ile Ser Gln Asn Ser Ile His Thr Tyr Tyr Ala Asn Ser Val
    50                  55                  60

Lys Gly Arg Phe Thr Ile Ser Arg Asp Asn Ser Lys Asn Thr Val Tyr
65                  70                  75                  80

Leu Gln Leu Asn Ser Leu Arg Pro Glu Asp Thr Ala Leu Tyr Tyr Cys
                85                  90                  95

Ala Ala Ser Arg Phe Thr Ser Trp Tyr Thr Ala Asp Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Leu Val Gln Ala Gly Gly Ser
                165                 170                 175

Leu Arg Leu Ser Cys Ala Ala Ser Gly Ile Thr Phe Ser Ile Asn Thr
            180                 185                 190

Met Gly Trp Tyr Arg Gln Ala Pro Gly Lys Gln Arg Glu Leu Val Ala
        195                 200                 205

Leu Ile Ser Ser Ile Gly Asp Thr Tyr Tyr Ala Asp Ser Val Lys Gly
    210                 215                 220

Arg Phe Thr Ile Ser Arg Asp Asn Ala Lys Asn Thr Val Tyr Leu Gln
225                 230                 235                 240

Met Asn Ser Leu Lys Pro Glu Asp Thr Ala Val Tyr Tyr Cys Lys Arg
```

```
                        245                 250                 255
Phe Arg Thr Ala Ala Gln Gly Thr Asp Tyr Trp Gly Gln Gly Thr Leu
                260                 265                 270

Val Thr Val Ser Ser Gly Gly Gly Gly Ser Gly Gly Gly Gly Ser Gly
            275                 280                 285

Gly Gly Gly Ser Gly Gly Gly Gly Ser Gly Gly Gly Gly Ser Gly Gly
        290                 295                 300

Gly Gly Ser Gly Gly Gly Ser Glu Val Gln Leu Val Glu Ser Gly
305                 310                 315                 320

Gly Gly Leu Val Gln Ala Gly Gly Ser Leu Arg Leu Ser Cys Ala Ala
                325                 330                 335

Ser Gly Ile Thr Phe Ser Ile Asn Thr Met Gly Trp Tyr Arg Gln Ala
            340                 345                 350

Pro Gly Lys Gln Arg Glu Leu Val Ala Leu Ile Ser Ser Ile Gly Asp
        355                 360                 365

Thr Tyr Tyr Ala Asp Ser Val Lys Gly Arg Phe Thr Ile Ser Arg Asp
    370                 375                 380

Asn Ala Lys Asn Thr Val Tyr Leu Gln Met Asn Ser Leu Lys Pro Glu
385                 390                 395                 400

Asp Thr Ala Val Tyr Tyr Cys Lys Arg Phe Arg Thr Ala Ala Gln Gly
                405                 410                 415

Thr Asp Tyr Trp Gly Gln Gly Thr Leu Val Thr Val Ser Ser Ala
            420                 425                 430

<210> SEQ ID NO 53
<211> LENGTH: 448
<212> TYPE: PRT
<213> ORGANISM: Artificial Sequence
<220> FEATURE:
<223> OTHER INFORMATION: trivalent construct

<400> SEQUENCE: 53

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Glu Val Gln Leu Val Glu Ser Gly Gly Val Val Gln Pro
                165                 170                 175

Gly Gly Ser Leu Arg Leu Ser Cys Ala Ala Ser Gly Arg Thr Phe Ser
```

180                 185                 190
Ser Tyr Ala Met Gly Trp Phe Arg Gln Ala Pro Gly Lys Glu Arg Glu
            195                 200                 205

Phe Val Ala Ala Ile Ser Trp Ser Asp Gly Ser Thr Tyr Tyr Ala Asp
        210                 215                 220

Ser Val Lys Gly Arg Phe Thr Ile Ser Arg Asp Asn Ala Lys Asn Thr
225                 230                 235                 240

Val Tyr Leu Gln Met Asn Ser Leu Arg Pro Glu Asp Thr Ala Leu Tyr
                245                 250                 255

Tyr Cys Ala Ala Asp Leu Thr Ser Thr Asn Pro Gly Ser Tyr Ile Tyr
            260                 265                 270

Ile Trp Ala Tyr Asp Tyr Trp Gly Gln Gly Thr Leu Val Thr Val Ser
        275                 280                 285

Ser Gly Gly Gly Gly Ser Gly Gly Gly Ser Gly Gly Gly Gly Ser
    290                 295                 300

Gly Gly Gly Gly Ser Gly Gly Gly Ser Gly Gly Gly Ser Gly
305                 310                 315                 320

Gly Gly Gly Ser Glu Val Gln Leu Val Glu Ser Gly Gly Val Val
                325                 330                 335

Gln Pro Gly Gly Ser Leu Arg Leu Ser Cys Ala Ala Ser Gly Gly Thr
            340                 345                 350

Phe Ser Thr Tyr Val Met Gly Trp Phe Arg Gln Ala Pro Gly Lys Glu
        355                 360                 365

Arg Glu Phe Val Ser Ala Ile Ser Gln Asn Ser Ile His Thr Tyr Tyr
    370                 375                 380

Ala Asn Ser Val Lys Gly Arg Phe Thr Ile Ser Arg Asp Asn Ser Lys
385                 390                 395                 400

Asn Thr Val Tyr Leu Gln Met Asn Ser Leu Arg Pro Glu Asp Thr Ala
                405                 410                 415

Leu Tyr Tyr Cys Ala Ala Ser Arg Phe Thr Ser Trp Tyr Thr Ala Asp
            420                 425                 430

Tyr Glu Tyr Asp Tyr Trp Gly Gln Gly Thr Leu Val Thr Val Ser Ser
        435                 440                 445

<210> SEQ ID NO 54
<211> LENGTH: 609
<212> TYPE: PRT
<213> ORGANISM: Homo sapiens

<400> SEQUENCE: 54

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

-continued

```
Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
```

```
                    530                 535                 540
Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                    565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 55
<211> LENGTH: 607
<212> TYPE: PRT
<213> ORGANISM: Mus musculus

<400> SEQUENCE: 55

Met Lys Trp Val Thr Phe Leu Leu Leu Leu Phe Val Ser Gly Ser Ala
1               5                   10                  15

Phe Ser Arg Gly Phe Arg Arg Glu Ala His Lys Ser Glu Ile Ala His
                20                  25                  30

Arg Tyr Asn Asp Leu Gly Glu Gln His Phe Lys Gly Leu Val Leu Ile
            35                  40                  45

Ala Phe Ser Gln Tyr Leu Gln Lys Cys Ser Tyr Asp Glu His Ala Lys
        50                  55                  60

Leu Val Gln Glu Val Thr Asp Phe Ala Lys Thr Cys Val Ala Asp Glu
65                  70                  75                  80

Ser Ala Ala Asn Cys Asp Lys Ser Leu His Thr Leu Phe Gly Asp Lys
                85                  90                  95

Leu Cys Ala Ile Pro Asn Leu Arg Glu Asn Tyr Gly Glu Leu Ala Asp
                100                 105                 110

Cys Cys Thr Lys Gln Glu Pro Glu Arg Asn Glu Cys Phe Leu Gln His
            115                 120                 125

Lys Asp Asp Asn Pro Ser Leu Pro Pro Phe Glu Arg Pro Glu Ala Glu
130                 135                 140

Ala Met Cys Thr Ser Phe Lys Glu Asn Pro Thr Thr Phe Met Gly His
145                 150                 155                 160

Tyr Leu His Glu Val Ala Arg Arg His Pro Tyr Phe Tyr Ala Pro Glu
                165                 170                 175

Leu Leu Tyr Tyr Ala Glu Gln Tyr Asn Glu Ile Leu Thr Gln Cys Cys
                180                 185                 190

Ala Glu Ala Asp Lys Glu Ser Cys Leu Thr Pro Lys Leu Asp Gly Val
            195                 200                 205

Lys Glu Lys Ala Leu Val Ser Ser Val Arg Gln Arg Met Lys Cys Ser
210                 215                 220

Ser Met Gln Lys Phe Gly Glu Arg Ala Phe Lys Ala Trp Ala Val Ala
225                 230                 235                 240

Arg Leu Ser Gln Thr Phe Pro Asn Ala Asp Phe Ala Glu Ile Thr Lys
                245                 250                 255

Leu Ala Thr Asp Leu Thr Lys Val Asn Lys Glu Cys Cys His Gly Asp
                260                 265                 270

Leu Leu Glu Cys Ala Asp Asp Arg Ala Glu Leu Ala Lys Tyr Met Cys
            275                 280                 285

Glu Asn Gln Ala Thr Ile Ser Ser Lys Leu Gln Thr Cys Cys Asp Lys
```

```
            290                 295                 300

Pro Leu Leu Lys Lys Ala His Cys Leu Ser Glu Val Glu His Asp Thr
305                 310                 315                 320

Met Pro Ala Asp Leu Pro Ala Ile Ala Ala Asp Phe Val Glu Asp Gln
                325                 330                 335

Glu Val Cys Lys Asn Tyr Ala Glu Ala Lys Asp Val Phe Leu Gly Thr
                340                 345                 350

Phe Leu Tyr Glu Tyr Ser Arg Arg His Pro Asp Tyr Ser Val Ser Leu
                355                 360                 365

Leu Leu Arg Leu Ala Lys Lys Tyr Glu Ala Thr Leu Glu Lys Cys Cys
            370                 375                 380

Ala Glu Ala Asn Pro Pro Ala Cys Tyr Gly Thr Val Leu Ala Glu Phe
385                 390                 395                 400

Gln Pro Leu Val Glu Glu Pro Lys Asn Leu Val Lys Thr Asn Cys Asp
                405                 410                 415

Leu Tyr Glu Lys Leu Gly Glu Tyr Gly Phe Gln Asn Ala Ile Leu Val
                420                 425                 430

Arg Tyr Thr Gln Lys Ala Pro Gln Val Ser Thr Pro Thr Leu Val Glu
                435                 440                 445

Ala Ala Arg Asn Leu Gly Arg Val Gly Thr Lys Cys Cys Thr Leu Pro
            450                 455                 460

Glu Asp Gln Arg Leu Pro Cys Val Glu Asp Tyr Leu Ser Ala Ile Leu
465                 470                 475                 480

Asn Arg Val Cys Leu Leu His Glu Lys Thr Pro Val Ser Glu His Val
                485                 490                 495

Thr Lys Cys Cys Ser Gly Ser Leu Val Glu Arg Arg Pro Cys Phe Ser
                500                 505                 510

Ala Leu Thr Val Asp Glu Thr Tyr Val Pro Lys Glu Phe Lys Ala Glu
                515                 520                 525

Thr Phe Thr Phe His Ser Asp Ile Cys Thr Leu Pro Glu Lys Glu Lys
                530                 535                 540

Gln Ile Lys Lys Gln Thr Ala Leu Ala Glu Leu Val Lys His Lys Pro
545                 550                 555                 560

Lys Ala Thr Ala Glu Gln Leu Lys Thr Val Met Asp Asp Phe Ala Gln
                565                 570                 575

Phe Leu Asp Thr Cys Cys Lys Ala Ala Asp Lys Asp Thr Cys Phe Ser
                580                 585                 590

Thr Glu Gly Pro Asn Leu Val Thr Arg Cys Lys Asp Ala Leu Ala
                595                 600                 605

<210> SEQ ID NO 56
<211> LENGTH: 608
<212> TYPE: PRT
<213> ORGANISM: Rattus norvegicus

<400> SEQUENCE: 56

Met Lys Trp Val Thr Phe Leu Leu Leu Leu Phe Ile Ser Gly Ser Ala
1               5                   10                  15

Phe Ser Arg Gly Val Phe Arg Arg Glu Ala His Lys Ser Glu Ile Ala
                20                  25                  30

His Arg Phe Lys Asp Leu Gly Glu Gln His Phe Lys Gly Leu Val Leu
            35                  40                  45

Ile Ala Phe Ser Gln Tyr Leu Gln Lys Cys Pro Tyr Glu Glu His Ile
        50                  55                  60
```

```
Lys Leu Val Gln Glu Val Thr Asp Phe Ala Lys Thr Cys Val Ala Asp
 65                  70                  75                  80

Glu Asn Ala Glu Asn Cys Asp Lys Ser Ile His Thr Leu Phe Gly Asp
                 85                  90                  95

Lys Leu Cys Ala Ile Pro Lys Leu Arg Asp Asn Tyr Gly Glu Leu Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Phe Gln Arg Pro Glu Ala
    130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

Cys Thr Glu Ser Asp Lys Ala Ala Cys Leu Thr Pro Lys Leu Asp Ala
        195                 200                 205

Val Lys Glu Lys Ala Leu Val Ala Ala Val Arg Gln Arg Met Lys Cys
    210                 215                 220

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
                245                 250                 255

Lys Leu Ala Thr Asp Leu Thr Lys Ile Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Ala Cys Cys Asp
    290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Gly Asp Pro Pro Ala Cys Tyr Gly Thr Val Leu Ala Glu
385                 390                 395                 400

Phe Gln Pro Leu Val Glu Pro Lys Asn Leu Val Lys Thr Asn Cys
                405                 410                 415

Glu Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
```

```
            485                 490                 495
Val Thr Lys Cys Cys Ser Gly Ser Leu Val Glu Arg Pro Cys Phe
            500                 505                 510

Ser Ala Leu Thr Val Asp Glu Thr Tyr Val Pro Lys Glu Phe Lys Ala
                515                 520                 525

Glu Thr Phe Thr Phe His Ser Asp Ile Cys Thr Leu Pro Asp Lys Glu
            530                 535                 540

Lys Gln Ile Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
                580                 585                 590

Ala Thr Glu Gly Pro Asn Leu Val Ala Arg Ser Lys Glu Ala Leu Ala
                595                 600                 605

<210> SEQ ID NO 57
<211> LENGTH: 607
<212> TYPE: PRT
<213> ORGANISM: Bos taurus

<400> SEQUENCE: 57

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Thr Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255
```

```
Leu Val Thr Asp Leu Thr Lys Val His Lys Glu Cys Cys His Gly Asp
            260                 265                 270
Leu Leu Glu Cys Ala Asp Asp Arg Ala Asp Leu Ala Lys Tyr Ile Cys
        275                 280                 285
Asp Asn Gln Asp Thr Ile Ser Ser Lys Leu Lys Glu Cys Cys Asp Lys
    290                 295                 300
Pro Leu Leu Glu Lys Ser His Cys Ile Ala Glu Val Glu Lys Asp Ala
305                 310                 315                 320
Ile Pro Glu Asn Leu Pro Pro Leu Thr Ala Asp Phe Ala Glu Asp Lys
                325                 330                 335
Asp Val Cys Lys Asn Tyr Gln Glu Ala Lys Asp Ala Phe Leu Gly Ser
            340                 345                 350
Phe Leu Tyr Glu Tyr Ser Arg Arg His Pro Glu Tyr Ala Val Ser Val
        355                 360                 365
Leu Leu Arg Leu Ala Lys Glu Tyr Glu Ala Thr Leu Glu Glu Cys Cys
    370                 375                 380
Ala Lys Asp Asp Pro His Ala Cys Tyr Ser Thr Val Phe Asp Lys Leu
385                 390                 395                 400
Lys His Leu Val Asp Glu Pro Gln Asn Leu Ile Lys Gln Asn Cys Asp
                405                 410                 415
Gln Phe Glu Lys Leu Gly Glu Tyr Gly Phe Gln Asn Ala Leu Ile Val
            420                 425                 430
Arg Tyr Thr Arg Lys Val Pro Gln Val Ser Thr Pro Thr Leu Val Glu
        435                 440                 445
Val Ser Arg Ser Leu Gly Lys Val Gly Thr Arg Cys Cys Thr Lys Pro
    450                 455                 460
Glu Ser Glu Arg Met Pro Cys Thr Glu Asp Tyr Leu Ser Leu Ile Leu
465                 470                 475                 480
Asn Arg Leu Cys Val Leu His Glu Lys Thr Pro Val Ser Glu Lys Val
                485                 490                 495
Thr Lys Cys Cys Thr Glu Ser Leu Val Asn Arg Arg Pro Cys Phe Ser
            500                 505                 510
Ala Leu Thr Pro Asp Glu Thr Tyr Val Pro Lys Ala Phe Asp Glu Lys
        515                 520                 525
Leu Phe Thr Phe His Ala Asp Ile Cys Thr Leu Pro Asp Thr Glu Lys
    530                 535                 540
Gln Ile Lys Lys Gln Thr Ala Leu Val Glu Leu Leu Lys His Lys Pro
545                 550                 555                 560
Lys Ala Thr Glu Glu Gln Leu Lys Thr Val Met Glu Asn Phe Val Ala
                565                 570                 575
Phe Val Asp Lys Cys Cys Ala Ala Asp Asp Lys Glu Ala Cys Phe Ala
            580                 585                 590
Val Glu Gly Pro Lys Leu Val Val Ser Thr Gln Thr Ala Leu Ala
        595                 600                 605

<210> SEQ ID NO 58
<211> LENGTH: 607
<212> TYPE: PRT
<213> ORGANISM: Sus scrofa

<400> SEQUENCE: 58

Met Lys Trp Val Thr Phe Ile Ser Leu Leu Phe Leu Phe Ser Ser Ala
1               5                   10                  15
Tyr Ser Arg Gly Val Phe Arg Arg Asp Thr Tyr Lys Ser Glu Ile Ala
            20                  25                  30
```

```
His Arg Phe Lys Asp Leu Gly Glu Gln Tyr Phe Lys Gly Leu Val Leu
         35                  40                  45

Ile Ala Phe Ser Gln His Leu Gln Gln Cys Pro Tyr Glu Glu His Val
 50                  55                  60

Lys Leu Val Arg Glu Val Thr Glu Phe Ala Lys Thr Cys Val Ala Asp
 65              70                  75                  80

Glu Ser Ala Glu Asn Cys Asp Lys Ser Ile His Thr Leu Phe Gly Asp
                 85                  90                  95

Lys Leu Cys Ala Ile Pro Ser Leu Arg Glu His Tyr Gly Asp Leu Ala
             100                 105                 110

Asp Cys Cys Glu Lys Glu Pro Glu Arg Asn Glu Cys Phe Leu Gln
             115                 120                 125

His Lys Asn Asp Asn Pro Asp Ile Pro Lys Leu Lys Pro Asp Pro Val
         130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
             165                 170                 175

Leu Leu Tyr Tyr Ala Ile Ile Tyr Lys Asp Val Phe Ser Glu Cys Cys
             180                 185                 190

Gln Ala Ala Asp Lys Ala Ala Cys Leu Leu Pro Lys Ile Glu His Leu
             195                 200                 205

Arg Glu Lys Val Leu Thr Ser Ala Ala Lys Gln Arg Leu Lys Cys Ala
         210                 215                 220

Ser Ile Gln Lys Phe Gly Glu Arg Ala Phe Lys Ala Trp Ser Leu Ala
225                 230                 235                 240

Arg Leu Ser Gln Arg Phe Pro Lys Ala Asp Phe Thr Glu Ile Ser Lys
                 245                 250                 255

Ile Val Thr Asp Leu Ala Lys Val His Lys Glu Cys Cys His Gly Asp
                 260                 265                 270

Leu Leu Glu Cys Ala Asp Asp Arg Ala Asp Leu Ala Lys Tyr Ile Cys
             275                 280                 285

Glu Asn Gln Asp Thr Ile Ser Thr Lys Leu Lys Glu Cys Cys Asp Lys
         290                 295                 300

Pro Leu Leu Glu Lys Ser His Cys Ile Ala Glu Ala Lys Arg Asp Glu
305                 310                 315                 320

Leu Pro Ala Asp Leu Asn Pro Leu Glu His Asp Phe Val Glu Asp Lys
                 325                 330                 335

Glu Val Cys Lys Asn Tyr Lys Glu Ala Lys His Val Phe Leu Gly Thr
                 340                 345                 350

Phe Leu Tyr Glu Tyr Ser Arg Arg His Pro Asp Tyr Ser Val Ser Leu
             355                 360                 365

Leu Leu Arg Ile Ala Lys Ile Tyr Glu Ala Thr Leu Glu Asp Cys Cys
         370                 375                 380

Ala Lys Glu Asp Pro Pro Ala Cys Tyr Ala Thr Val Phe Asp Lys Phe
385                 390                 395                 400

Gln Pro Leu Val Asp Glu Pro Lys Asn Leu Ile Lys Gln Asn Cys Glu
                 405                 410                 415

Leu Phe Glu Lys Leu Gly Glu Tyr Gly Phe Gln Asn Ala Leu Ile Val
             420                 425                 430

Arg Tyr Thr Lys Lys Val Pro Gln Val Ser Thr Pro Thr Leu Val Glu
         435                 440                 445
```

-continued

```
Val Ala Arg Lys Leu Gly Leu Val Gly Ser Arg Cys Cys Lys Arg Pro
            450                 455                 460

Glu Glu Glu Arg Leu Ser Cys Ala Glu Asp Tyr Leu Ser Leu Val Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Lys Pro Lys Glu Phe Val Glu Gly
                515                 520                 525

Thr Phe Thr Phe His Ala Asp Leu Cys Thr Leu Pro Glu Asp Glu Lys
            530                 535                 540

Gln Ile Lys Lys Gln Thr Ala Leu Val Glu Leu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
            580                 585                 590

Val Glu Gly Pro Lys Phe Val Ile Glu Ile Arg Gly Ile Leu Ala
                595                 600                 605

<210> SEQ ID NO 59
<211> LENGTH: 608
<212> TYPE: PRT
<213> ORGANISM: Canis lupus

<400> SEQUENCE: 59

Met Lys Trp Val Thr Phe Ile Ser Leu Phe Phe Leu Phe Ser Ser Ala
1               5                   10                  15

Tyr Ser Arg Gly Leu Val Arg Arg Glu Ala Tyr Lys Ser Glu Ile Ala
                20                  25                  30

His Arg Tyr Asn Asp Leu Gly Glu Glu His Phe Arg Gly Leu Val Leu
            35                  40                  45

Val Ala Phe Ser Gln Tyr Leu Gln Gln Cys Pro Phe Glu Asp His Val
50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
                85                  90                  95

Lys Leu Cys Thr Val Ala Ser Leu Arg Asp Lys Tyr Gly Asp Met Ala
            100                 105                 110

Asp Cys Cys Glu Lys Gln Glu Pro Asp Arg Asn Glu Cys Phe Leu Ala
        115                 120                 125

His Lys Asp Asp Asn Pro Gly Phe Pro Pro Leu Val Ala Pro Glu Pro
130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Gln Gln Tyr Lys Gly Val Phe Ala Glu Cys
            180                 185                 190

Cys Gln Ala Ala Asp Lys Ala Ala Cys Leu Gly Pro Lys Ile Glu Ala
        195                 200                 205

Leu Arg Glu Lys Val Leu Leu Ser Ser Ala Lys Glu Arg Phe Lys Cys
210                 215                 220
```

```
Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
            245                 250                 255

Lys Val Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Thr Lys Leu Lys Glu Cys Cys Asp
        290                 295                 300

Lys Pro Val Leu Glu Lys Ser Gln Cys Leu Ala Glu Val Glu Arg Asp
305                 310                 315                 320

Glu Leu Pro Gly Asp Leu Pro Ser Leu Ala Ala Asp Phe Val Glu Asp
                325                 330                 335

Lys Glu Val Cys Lys Asn Tyr Gln Glu Ala Lys Asp Val Phe Leu Gly
            340                 345                 350

Thr Phe Leu Tyr Glu Tyr Ala Arg Arg His Pro Glu Tyr Ser Val Ser
        355                 360                 365

Leu Leu Leu Arg Leu Ala Lys Glu Tyr Glu Ala Thr Leu Glu Lys Cys
370                 375                 380

Cys Ala Thr Asp Asp Pro Pro Thr Cys Tyr Ala Lys Val Leu Asp Glu
385                 390                 395                 400

Phe Lys Pro Leu Val Asp Glu Pro Gln Asn Leu Val Lys Thr Asn Cys
                405                 410                 415

Glu Leu Phe Glu Lys Leu Gly Glu Tyr Gly Phe Gln Asn Ala Leu Leu
            420                 425                 430

Val Arg Tyr Thr Lys Lys Ala Pro Gln Val Ser Thr Pro Thr Leu Val
        435                 440                 445

Glu Val Ser Arg Lys Leu Gly Lys Val Gly Thr Lys Cys Cys Lys Lys
        450                 455                 460

Pro Glu Ser Glu Arg Met Ser Cys Ala Glu Asp Phe Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Ser Glu Ser Leu Val Asn Arg Arg Pro Cys Phe
            500                 505                 510

Ser Gly Leu Glu Val Asp Glu Thr Tyr Val Pro Lys Glu Phe Asn Ala
        515                 520                 525

Glu Thr Phe Thr Phe His Ala Asp Leu Cys Thr Leu Pro Glu Ala Glu
        530                 535                 540

Lys Gln Val Lys Gln Thr Ala Leu Val Glu Leu Leu Lys His Lys
545                 550                 555                 560

Pro Lys Ala Thr Asp Glu Gln Leu Lys Thr Val Met Gly Asp Phe Gly
                565                 570                 575

Ala Phe Val Glu Lys Cys Cys Ala Ala Glu Asn Lys Glu Gly Cys Phe
            580                 585                 590

Ser Glu Glu Gly Pro Lys Leu Val Ala Ala Gln Ala Ala Leu Val
        595                 600                 605

<210> SEQ ID NO 60
<211> LENGTH: 608
<212> TYPE: PRT
<213> ORGANISM: Felis catus
```

```
<400> SEQUENCE: 60

Met Lys Trp Val Thr Phe Ile Ser Leu Leu Leu Phe Ser Ser Ala
1               5                   10                  15

Tyr Ser Arg Gly Val Thr Arg Glu Ala His Gln Ser Glu Ile Ala
            20                  25                  30

His Arg Phe Asn Asp Leu Gly Glu Glu His Phe Arg Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Gly Cys Val Ala Asp
65                  70                  75                  80

Gln Ser Ala Ala Asn Cys Glu Lys Ser Leu His Glu Leu Leu Gly Asp
                85                  90                  95

Lys Leu Cys Thr Val Ala Ser Leu Arg Asp Lys Tyr Gly Glu Met Ala
            100                 105                 110

Asp Cys Cys Glu Lys Lys Glu Pro Glu Arg Asn Glu Cys Phe Leu Gln
        115                 120                 125

His Lys Asp Asp Asn Pro Gly Phe Gly Gln Leu Val Thr Pro Glu Ala
    130                 135                 140

Asp Ala Met Cys Thr Ala Phe His Glu Asn Glu Gln Arg Phe Leu Gly
145                 150                 155                 160

Lys Tyr Leu Tyr Glu Ile Ala Arg Arg His Pro Tyr Phe Tyr Ala Pro
            165                 170                 175

Glu Leu Leu Tyr Tyr Ala Glu Glu Tyr Lys Gly Val Phe Thr Glu Cys
        180                 185                 190

Cys Glu Ala Ala Asp Lys Ala Ala Cys Leu Thr Pro Lys Val Asp Ala
    195                 200                 205

Leu Arg Glu Lys Val Leu Ala Ser Ser Ala Lys Glu Arg Leu Lys Cys
210                 215                 220

Ala Ser Leu Gln Lys Phe Gly Glu Arg Ala Phe Lys Ala Trp Ser Val
225                 230                 235                 240

Ala Arg Leu Ser Gln Lys Phe Pro Lys Ala Glu Phe Ala Glu Ile Ser
            245                 250                 255

Lys Leu Val Thr Asp Leu Ala Lys Ile His Lys Glu Cys Cys His Gly
        260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Thr Lys Leu Lys Glu Cys Cys Gly
290                 295                 300

Lys Pro Val Leu Glu Lys Ser His Cys Ile Ser Glu Val Glu Arg Asp
305                 310                 315                 320

Glu Leu Pro Ala Asp Leu Pro Pro Leu Ala Val Asp Phe Val Glu Asp
            325                 330                 335

Lys Glu Val Cys Lys Asn Tyr Gln Glu Ala Lys Asp Val Phe Leu Gly
        340                 345                 350

Thr Phe Leu Tyr Glu Tyr Ser Arg Arg His Pro Glu Tyr Ser Val Ser
    355                 360                 365

Leu Leu Leu Arg Leu Ala Lys Glu Tyr Glu Ala Thr Leu Glu Lys Cys
370                 375                 380

Cys Ala Thr Asp Asp Pro Pro Ala Cys Tyr Ala His Val Phe Asp Glu
385                 390                 395                 400

Phe Lys Pro Leu Val Glu Glu Pro His Asn Leu Val Lys Thr Asn Cys
            405                 410                 415
```

Glu Leu Phe Glu Lys Leu Gly Glu Tyr Gly Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Ser Leu Gly Lys Val Gly Ser Lys Cys Cys Thr His
                450                 455                 460

Pro Glu Ala Glu Arg Leu Ser Cys Ala Glu Asp Tyr Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Thr Glu Ser Leu Val Asn Arg Arg Pro Cys Phe
                500                 505                 510

Ser Ala Leu Gln Val Asp Glu Thr Tyr Val Pro Lys Glu Phe Ser Ala
                515                 520                 525

Glu Thr Phe Thr Phe His Ala Asp Leu Cys Thr Leu Pro Glu Ala Glu
                530                 535                 540

Lys Gln Ile Lys Lys Gln Ser Ala Leu Val Glu Leu Leu Lys His Lys
545                 550                 555                 560

Pro Lys Ala Thr Glu Glu Gln Leu Lys Thr Val Met Gly Asp Phe Gly
                565                 570                 575

Ser Phe Val Asp Lys Cys Cys Ala Ala Glu Asp Lys Glu Ala Cys Phe
                580                 585                 590

Ala Glu Glu Gly Pro Lys Leu Val Ala Ala Gln Ala Ala Leu Ala
                595                 600                 605

<210> SEQ ID NO 61
<211> LENGTH: 607
<212> TYPE: PRT
<213> ORGANISM: Ovis aries

<400> SEQUENCE: 61

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Asn Asp Leu Gly Glu Glu Asn Phe Gln Gly Leu Val Leu
                35                  40                  45

Ile Ala Phe Ser Gln Tyr Leu Gln Gln Cys Pro Phe Asp Glu His Val
            50                  55                  60

Lys Leu Val Lys Glu Leu Thr Glu Phe Ala Lys Thr Cys Val Ala Asp
65                  70                  75                  80

Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
                100                 105                 110

Asp Cys Cys Glu Lys Gln Glu Pro Glu Arg Asn Glu Cys Phe Leu Asn
                115                 120                 125

His Lys Asp Asp Ser Pro Asp Leu Pro Lys Leu Lys Pro Glu Pro Asp
                130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys

-continued

```
            180             185                 190
Gln Ala Glu Asp Lys Gly Ala Cys Leu Leu Pro Lys Ile Asp Ala Met
            195                 200             205
Arg Glu Lys Val Leu Ala Ser Ser Ala Arg Gln Arg Leu Arg Cys Ala
        210                 215             220
Ser Ile Gln Lys Phe Gly Glu Arg Ala Leu Lys Ala Trp Ser Val Ala
225                 230                 235                 240
Arg Leu Ser Gln Lys Phe Pro Lys Ala Asp Phe Thr Asp Val Thr Lys
                245                 250                 255
Ile Val Thr Asp Leu Thr Lys Val His Lys Glu Cys Cys His Gly Asp
            260                 265                 270
Leu Leu Glu Cys Ala Asp Asp Arg Ala Asp Leu Ala Lys Tyr Ile Cys
            275                 280                 285
Asp His Gln Asp Ala Leu Ser Ser Lys Leu Lys Glu Cys Cys Asp Lys
        290                 295                 300
Pro Val Leu Glu Lys Ser His Cys Ile Ala Glu Val Asp Lys Asp Ala
305                 310                 315                 320
Val Pro Glu Asn Leu Pro Pro Leu Thr Ala Asp Phe Ala Glu Asp Lys
                325                 330                 335
Glu Val Cys Lys Asn Tyr Gln Glu Ala Lys Asp Val Phe Leu Gly Ser
            340                 345                 350
Phe Leu Tyr Glu Tyr Ser Arg Arg His Pro Glu Tyr Ala Val Ser Val
            355                 360                 365
Leu Leu Arg Leu Ala Lys Glu Tyr Glu Ala Thr Leu Glu Asp Cys Cys
        370                 375                 380
Ala Lys Glu Asp Pro His Ala Cys Tyr Ala Thr Val Phe Asp Lys Leu
385                 390                 395                 400
Lys His Leu Val Asp Glu Pro Gln Asn Leu Ile Lys Lys Asn Cys Glu
                405                 410                 415
Leu Phe Glu Lys His Gly Glu Tyr Gly Phe Gln Asn Ala Leu Ile Val
            420                 425                 430
Arg Tyr Thr Arg Lys Ala Pro Gln Val Ser Thr Pro Thr Leu Val Glu
            435                 440                 445
Ile Ser Arg Ser Leu Gly Lys Val Gly Thr Lys Cys Cys Ala Lys Pro
        450                 455                 460
Glu Ser Glu Arg Met Pro Cys Thr Glu Asp Tyr Leu Ser Leu Ile Leu
465                 470                 475                 480
Asn Arg Leu Cys Val Leu His Glu Lys Thr Pro Val Ser Glu Lys Val
                485                 490                 495
Thr Lys Cys Cys Thr Glu Ser Leu Val Asn Arg Arg Pro Cys Phe Ser
            500                 505                 510
Asp Leu Thr Leu Asp Glu Thr Tyr Val Pro Lys Pro Phe Asp Glu Lys
            515                 520                 525
Phe Phe Thr Phe His Ala Asp Ile Cys Thr Leu Pro Asp Thr Glu Lys
        530                 535                 540
Gln Ile Lys Lys Gln Thr Ala Leu Val Glu Leu Leu Lys His Lys Pro
545                 550                 555                 560
Lys Ala Thr Asp Glu Gln Leu Lys Thr Val Met Glu Asn Phe Val Ala
                565                 570                 575
Phe Val Asp Lys Cys Cys Ala Ala Asp Asp Lys Glu Gly Cys Phe Val
            580                 585                 590
Leu Glu Gly Pro Lys Leu Val Ala Ser Thr Gln Ala Ala Leu Ala
            595                 600                 605
```

<210> SEQ ID NO 62
<211> LENGTH: 607
<212> TYPE: PRT
<213> ORGANISM: Equus caballus

<400> SEQUENCE: 62

Met Lys Trp Val Thr Phe Val Ser Leu Leu Phe Leu Phe Ser Ser Ala
1               5                   10                  15

Tyr Ser Arg Gly Val Leu Arg Arg Asp Thr His Lys Ser Glu Ile Ala
            20                  25                  30

His Arg Phe Asn Asp Leu Gly Glu Lys His Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Leu Ala Cys Leu Ile Pro Lys Leu Asp Ala Leu
        195                 200                 205

Lys Glu Arg Ile Leu Leu Ser Ser Ala Lys Glu Arg Leu Lys Cys Ser
    210                 215                 220

Ser Phe Gln Asn Phe Gly Glu Arg Ala Val Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Thr Tyr Glu Ala Thr Leu Glu Lys Cys Cys

```
                370                375                380
Ala Glu Ala Asp Pro Pro Ala Cys Tyr Arg Thr Val Phe Asp Gln Phe
385                390                395                400

Thr Pro Leu Val Glu Glu Pro Lys Ser Leu Val Lys Lys Asn Cys Asp
                405                410                415

Leu Phe Glu Glu Val Gly Glu Tyr Asp Phe Gln Asn Ala Leu Ile Val
            420                425                430

Arg Tyr Thr Lys Lys Ala Pro Gln Val Ser Thr Pro Thr Leu Val Glu
            435                440                445

Ile Gly Arg Thr Leu Gly Lys Val Gly Ser Arg Cys Cys Lys Leu Pro
        450                455                460

Glu Ser Glu Arg Leu Pro Cys Ser Glu Asn His Leu Ala Leu Ala Leu
465                470                475                480

Asn Arg Leu Cys Val Leu His Glu Lys Thr Pro Val Ser Glu Lys Ile
                485                490                495

Thr Lys Cys Cys Thr Asp Ser Leu Ala Glu Arg Arg Pro Cys Phe Ser
            500                505                510

Ala Leu Glu Leu Asp Glu Gly Tyr Val Pro Lys Glu Phe Lys Ala Glu
            515                520                525

Thr Phe Thr Phe His Ala Asp Ile Cys Thr Leu Pro Glu Asp Glu Lys
            530                535                540

Gln Ile Lys Lys Gln Ser Ala Leu Ala Glu Leu Val Lys His Lys Pro
545                550                555                560

Lys Ala Thr Lys Glu Gln Leu Lys Thr Val Leu Gly Asn Phe Ser Ala
                565                570                575

Phe Val Ala Lys Cys Cys Gly Arg Glu Asp Lys Glu Ala Cys Phe Ala
            580                585                590

Glu Glu Gly Pro Lys Leu Val Ala Ser Ser Gln Leu Ala Leu Ala
            595                600                605

<210> SEQ ID NO 63
<211> LENGTH: 608
<212> TYPE: PRT
<213> ORGANISM: Oryctolagus cuniculus

<400> SEQUENCE: 63

Met Lys Trp Val Thr Phe Ile Ser Leu Leu Phe Leu Phe Ser Ser Ala
1               5                   10                  15

Tyr Ser Arg Gly Val Phe Arg Arg Glu Ala His Lys Ser Glu Ile Ala
                20                  25                  30

His Arg Phe Asn Asp Val Gly Glu His Phe Ile Gly Leu Val Leu
            35                  40                  45

Ile Thr Phe Ser Gln Tyr Leu Gln Lys Cys Pro Tyr Glu Glu His Ala
        50                  55                  60

Lys Leu Val Lys Glu Val Thr Asp Leu Ala Lys Ala Cys Val Ala Asp
65                  70                  75                  80

Glu Ser Ala Ala Asn Cys Asp Lys Ser Leu His Asp Ile Phe Gly Asp
                85                  90                  95

Lys Ile Cys Ala Leu Pro Ser Leu Arg Asp Thr Tyr Gly Asp Val Ala
            100                 105                 110

Asp Cys Cys Glu Lys Lys Glu Pro Glu Arg Asn Glu Cys Phe Leu His
            115                 120                 125

His Lys Asp Asp Lys Pro Asp Leu Pro Pro Phe Ala Arg Pro Glu Ala
            130                 135                 140
```

-continued

```
Asp Val Leu Cys Lys Ala Phe His Asp Asp Glu Lys Ala Phe Phe Gly
145                 150                 155                 160
His Tyr Leu Tyr Glu Val Ala Arg Arg His Pro Tyr Phe Tyr Ala Pro
            165                 170                 175
Glu Leu Leu Tyr Tyr Ala Gln Lys Tyr Lys Ala Ile Leu Thr Glu Cys
            180                 185                 190
Cys Glu Ala Ala Asp Lys Gly Ala Cys Leu Thr Pro Lys Leu Asp Ala
            195                 200                 205
Leu Glu Gly Lys Ser Leu Ile Ser Ala Ala Gln Glu Arg Leu Arg Cys
            210                 215                 220
Ala Ser Ile Gln Lys Phe Gly Asp Arg Ala Tyr Lys Ala Trp Ala Leu
225                 230                 235                 240
Val Arg Leu Ser Gln Arg Phe Pro Lys Ala Asp Phe Thr Asp Ile Ser
            245                 250                 255
Lys Ile Val Thr Asp Leu Thr Lys Val His Lys Glu Cys Cys His Gly
            260                 265                 270
Asp Leu Leu Glu Cys Ala Asp Asp Arg Ala Asp Leu Ala Lys Tyr Met
            275                 280                 285
Cys Glu His Gln Glu Thr Ile Ser Ser His Leu Lys Glu Cys Cys Asp
290                 295                 300
Lys Pro Ile Leu Glu Lys Ala His Cys Ile Tyr Gly Leu His Asn Asp
305                 310                 315                 320
Glu Thr Pro Ala Gly Leu Pro Ala Val Ala Glu Glu Phe Val Glu Asp
            325                 330                 335
Lys Asp Val Cys Lys Asn Tyr Glu Glu Ala Lys Asp Leu Phe Leu Gly
            340                 345                 350
Lys Phe Leu Tyr Glu Tyr Ser Arg Arg His Pro Asp Tyr Ser Val Val
            355                 360                 365
Leu Leu Leu Arg Leu Gly Lys Ala Tyr Glu Ala Thr Leu Lys Lys Cys
            370                 375                 380
Cys Ala Thr Asp Asp Pro His Ala Cys Tyr Ala Lys Val Leu Asp Glu
385                 390                 395                 400
Phe Gln Pro Leu Val Asp Glu Pro Lys Asn Leu Val Lys Gln Asn Cys
            405                 410                 415
Glu Leu Tyr Glu Gln Leu Gly Asp Tyr Asn Phe Gln Asn Ala Leu Leu
            420                 425                 430
Val Arg Tyr Thr Lys Lys Val Pro Gln Val Ser Thr Pro Thr Leu Val
            435                 440                 445
Glu Ile Ser Arg Ser Leu Gly Lys Val Gly Ser Lys Cys Cys Lys His
450                 455                 460
Pro Glu Ala Glu Arg Leu Pro Cys Val Glu Asp Tyr Leu Ser Val Val
465                 470                 475                 480
Leu Asn Arg Leu Cys Val Leu His Glu Lys Thr Pro Val Ser Glu Lys
            485                 490                 495
Val Thr Lys Cys Cys Ser Glu Ser Leu Val Asp Arg Arg Pro Cys Phe
            500                 505                 510
Ser Ala Leu Gly Pro Asp Glu Thr Tyr Val Pro Lys Glu Phe Asn Ala
            515                 520                 525
Glu Thr Phe Thr Phe His Ala Asp Ile Cys Thr Leu Pro Glu Thr Glu
            530                 535                 540
Arg Lys Ile Lys Lys Gln Thr Ala Leu Val Glu Leu Val Lys His Lys
545                 550                 555                 560
```

```
Pro His Ala Thr Asn Asp Gln Leu Lys Thr Val Val Gly Glu Phe Thr
                565                 570                 575

Ala Leu Leu Asp Lys Cys Cys Ser Ala Glu Asp Lys Glu Ala Cys Phe
                580                 585                 590

Ala Val Glu Gly Pro Lys Leu Val Glu Ser Ser Lys Ala Thr Leu Gly
        595                 600                 605
```

SERUM ALBUMIN BINDERS

RELATED APPLICATIONS

This application is a national stage filing under 35 U.S.C. § 371 of International Patent Application PCT/EP2018/051083, filed Jan. 17, 2018, which claims priority under 35 U.S.C § 119(e) to U.S. Provisional Application Ser. No. 62/446,988, filed Jan. 17, 2017, the entire contents of each of which are incorporated herein in their entirety.

The present invention relates to amino acid sequences that can bind to serum albumin.

In particular, the present invention relates to immunoglobulin single variable domains, and in particular heavy-chain immunoglobulin single variable domains, that can bind to serum albumin.

As described herein, the immunoglobulin single variable domains provided by the invention are preferably such that they can (at least) bind (and in particular, specifically bind) to human serum albumin. More preferably, as further described herein, these immunoglobulin single variable domains are preferably further such that they are cross-reactive (as described herein) between human serum albumin and serum albumin from at least one other species of mammal.

The invention also relates to proteins, polypeptides and other constructs, compounds, molecules or chemical entities that comprise at least one of the immunoglobulin single variable domains binding to serum albumin that are described herein.

Immunoglobulin single variable domains will also generally be referred to herein by means of the abbreviations "ISV's" or "ISVD's" (which will be used interchangeably herein).

The immunoglobulin single variable domains binding to serum albumin that are described herein will also be referred to herein as "amino acid sequences of the invention", or "serum albumin binders of the invention". As further described herein, the albumin binders of the invention may in particular be Nanobodies (as further described herein).

The proteins, polypeptides and other constructs, compounds, molecules or chemical entities that comprise at least one of the serum albumin binder of the invention will also referred to herein as "compounds of the invention" or as "polypeptides of the invention". Preferably, the compounds of the invention are proteins or polypeptides, and may in particular be fusion proteins.

Other aspects, embodiments, features, uses and advantages of the invention will be clear to the skilled person based on the disclosure herein.

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regard to the CDR's, as is well-known in the art, there are multiple conventions to define and describe the CDR's of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/. For the purposes of the present specification and claims, even though the CDRs according to Kabat may also be mentioned, the CDRs are most preferably defined on the basis of the Abm definition (which is based on Oxford Molecular's AbM antibody modelling software), as this is considered to be an optimal compromise between the Kabat and Chothia definitions. Reference is again made to the website http://www.bioinforg.uk/abs/).

Accordingly, in the present specification and claims, all CDRs are defined according to the Abm convention, unless explicitly stated otherwise herein.

ISVD's (and in particular Nanobodies) that can bind to serum albumin and their uses are well-known in the art, for example from WO 2004/041865, WO 2006/122787, WO 2012/175400, WO 2015/173325 and PCT/EP2016/077973, which describe serum albumin-binding ISVD's and their use for extending the serum half-life (as defined in these applications) of therapeutic compounds, moieties and entities. For example, WO 2006/122787 discloses as SEQ ID NO: 62 a humanized serum albumin-binding Nanobody called Alb-8 (see SEQ ID NO:1 herein). WO 2012/175400 discloses as SEQ ID NO: 6 a humanized serum albumin-binding Nanobody called Alb-23D (see SEQ ID NO:2 herein). The amino acid sequences of Alb-8 and Alb-23D and their CDR's (which are the same for Alb-8 and Alb-23D) are given in Table A below as SEQ ID NO: 1, 2 and 3 to 8, respectively.

Some other references that disclose ISVD's against serum albumin include WO 2003/035694, WO 2004/003019, EP 2 139 918, WO 2011/006915 and WO 2014/111550.

FIGS. 3A and 3B show alignments of Alb-8 (reference), Alb-23D (reference), SEQ ID NO: 18 (invention) and SEQ ID NO: 19 (invention).

The present invention aims to provide improved serum albumin binders, and in particular serum albumin binders that have improved properties compared to the serum albumin binders known in the art. In particular, the invention aims to provide serum albumin binders that can bind to dog serum albumin and/or that have improved cross-reactivity between human serum albumin and dog serum albumin (i.e. compared to prior art serum albumin binders like Alb-8 and/or Alb-23D).

TABLE A

Alb-8, Alb-23D and their CDRs

| SEQ ID NO | Description | Sequence |
|---|---|---|
| 1 | Alb-8 (WO 2006/122787; SEQ ID NO: 62) | EVQLVESGGGLVQPGNSLRLSCAASGFTFSSFGMS WVRQAPGKGLEWVSSISGSGSDTLYADSVKGRFTI SRDNAKTTLYLQMNSLRPEDTAVYYCTIGGSLSRSS QGTLVTVSS |

TABLE A-continued

Alb-8, Alb-23D and their CDRs

| SEQ ID NO | Description | Sequence |
|---|---|---|
| 2 | Alb-23D (WO 2012/175400; SEQ ID NO: 6) | EVQLLESGGGLVQPGGSLRLSCAASGFTFRSFGMS WVRQAPGKGPEWVSSISGSGSDTLYADSVKGRFTI SRDNSKNTLYLQMNSLRPEDTAVYYCTIGGSLSRSS QGTLVTVSSA |
| 3 | CDR1 (Kabat) | SFGMS |
| 4 | CDR2 (Kabat) | SISGSGSDTLYADSVKG |
| 5 | CDR3 (Kabat/Abm) | GGSLSR |
| 6 | CDR1 (Abm) | GFTFRSFGMS |
| 7 | CDR2 (Abm) | SISGSGSDTL |
| 8 | CDR3 (Kabat/Abm) | GGSLSR |

Note:
SEQ ID NOs: 1 and 2 share the same CDRs according to Kabat. However, if the CDRs are defined under the Abm convention, SEQ ID NO: 1 has a different CDR1 from SEQ ID NOs: 2 compared to SEQ ID NOs: 2, SEQ ID NO: 1 has an S at position 30 instead of an R.
SEQ ID NO: 5 and SEQ ID NO: 8 are identical.
all CDRs are defined according to the Abm convention, unless indicated otherwise.

TABLE B

SEQ ID NOs: 18 and 19 and their CDR's

| SEQ ID NO | Description | Sequence |
|---|---|---|
| 18 | T0235002C06 (wild type) | EVQLVESGGGLVQTGDSLRLSCAASGGTFSTYVMGWFR QAPGKEREFVSAISQNSIHTYYANSVKGRFTISRDNDKNT VYLQLNSLKPEDTAVYYCAASRFTSWYTADYEYDYWG QGTLVTVSS |
| 19 | T023500029 | EVQLVESGGGVVQPGDSLRLSCAASGGTFSTYVMGWFR QAPGKEREFVSAISQNSIHTYYANSVKGRFTISRDNSKNT VYLQLNSLRPEDTALYYCAASRFTSWYTADYEYDYWG QGTLVTVSS |
| 9 | CDR1 (Kabat) | TYVMG |
| 10 | CDR2 (Kabat) | AISQNSIHTYYANSVKG |
| 11 | CDR2 (Kabat) | AISQNSIHTYYADSVKG |
| 12 | CDR1 (Abm) | GGTFSTYVMG |
| 13 | CDR2 (Abm) | AISQNSIHTY |
| 14 | CDR3 (Kabat/Abm) | SRFTSWYTADYEYDY |

Note:
all CDRs are defined according to the Abm convention, unless indicated otherwise.

Generally, the serum albumin-binding ISVD's provided by the present invention are variants of the sequences of SEQ ID NO:18 and 19, in that:
they have the same CDRs (or essentially the same CDR's) as the sequence of SEQ ID NO:18 and/or 19 (with the proviso that, if the CDRs are defined according to Kabat, CDR2 can be AISQNSIHTYYANSVKG (SEQ ID NO:10) or AISQNSIHTYYADSVKG (SEQ ID NO:11)); and
they have a certain degree of sequence identity with the sequence of SEQ ID NO:18 and/or 19 (which degree of sequence identity is as further described herein).

In particular, serum albumin-binding ISVD's provided by the present invention will generally have a (limited) number of "amino acid differences" (as described herein) compared to the sequence of SEQ ID NO:18 and/or 19. These amino acid differences may be present in the CDR's (as long as the resulting amino acid sequences as such that they retain the further properties of the amino acid sequences of the invention that are set out herein) and/or be present in the framework regions, and may in particular be present in the framework regions (as defined according to Kabat and/or according to Abm). For example and without limitation, these amino acid differences may for example be humanizing substitutions, substitutions that improve expression in a desired host cell or host organism, substitutions that improve stability and/or resistance to degradation and/or proteases, mutations that reduce binding by pre-existing antibodies, and/or other mutations that are intended to optimize the sequence of the amino acid sequences of the invention; or any suitable combination of such amino acid differences. Reference is made to the further disclosure herein.

In a first aspect, the invention relates to an ISVD that can bind (and in particular, specifically bind) to human serum albumin, and that has:

- a CDR1 (according to Kabat) that is the amino acid sequence TYVMG (SEQ ID NO: 9) or an amino acid sequence that has 2 or 1 amino acid difference(s) (as defined herein) with the amino acid sequence of SEQ ID NO: 9; and
- a CDR2 (according to Kabat) that is the amino acid sequence AISQNSIHTYYANSVKG (SEQ ID NO:10) or AISQNSIHTYYADSVKG (SEQ ID NO:11) or an amino acid sequence that has 3, 2 or 1 amino acid difference(s) (as defined herein) with the amino acid sequence of SEQ ID NO: 10 and/or SEQ ID NO:11; and
- a CDR3 (according to Kabat) that is the amino acid sequence SRFTSWYTADYEYDY (SEQ ID NO: 14) or an amino acid sequence that has 3, 2 or 1 amino acid difference(s) (as defined herein) with the amino acid sequence of SEQ ID NO: 14.

In particular, a serum albumin binder according to this aspect of the invention may be (and preferably is) as further described herein.

In a more specific aspect, the invention relates to an ISVD that can bind (and in particular, specifically bind) to human serum albumin, and that has:

- a CDR1 (according to Kabat) that is the amino acid sequence TYVMG (SEQ ID NO: 9); and
- a CDR2 (according to Kabat) that is the amino acid sequence AISQNSIHTYYANSVKG (SEQ ID NO:10) or AISQNSIHTYYADSVKG (SEQ ID NO:11); and
- a CDR3 (according to Kabat) that is the amino acid sequence SRFTSWYTADYEYDY (SEQ ID NO: 14).

Again, a serum albumin binder according to this aspect of the invention may be (and preferably is) as further described herein.

In another aspect, the invention relates to an ISVD that can bind (and in particular, specifically bind) to human serum albumin, and that has:

- a CDR1 (according to Abm) that is the amino acid sequence GGTFSTYVMG (SEQ ID NO: 12) or an amino acid sequence that has 2 or 1 amino acid difference(s) (as defined herein) with the amino acid sequence of SEQ ID NO: 12; and
- a CDR2 (according to Abm) that is the amino acid sequence AISQNSIHTY (SEQ ID NO: 13) or an amino acid sequence that has 3, 2 or 1 amino acid difference(s) (as defined herein) with the amino acid sequence of SEQ ID NO: 13; and
- a CDR3 (according to Abm) that is the amino acid sequence SRFTSWYTADYEYDY (SEQ ID NO: 14) or an amino acid sequence that has 3, 2 or 1 amino acid difference(s) (as defined herein) with the amino acid sequence of SEQ ID NO: 14.

In particular, a serum albumin binder according to this aspect of the invention may be (and preferably is) as further described herein.

In a more specific aspect, the invention relates to an ISVD that can bind (and in particular, specifically bind) to human serum albumin, and that has:

- a CDR1 (according to Abm) that is the amino acid sequence GGTFSTYVMG (SEQ ID NO: 12); and
- a CDR2 (according to Abm) that is the amino acid sequence AISQNSIHTY (SEQ ID NO: 13); and
- a CDR3 (according to Abm) that is the amino acid sequence SRFTSWYTADYEYDY (SEQ ID NO: 14).

Again, a serum albumin binder according to this aspect of the invention may be (and preferably is) as further described herein.

Generally, the serum albumin binders according to the different aspects of the invention are preferably such that they have:

- a degree of sequence identity with the sequence of SEQ ID NO: 18 and/or 19 (in which the CDR's and any C-terminal extension that may be present are not taken into account for determining the degree of sequence identity) of at least 85%, preferably at least 90%, more preferably at least 95%;

and/or such that they have:

- and/or have no more than 7, preferably no more than 5, such as only 3, 2 or 1 "amino acid differences" (as defined herein, and not taking into account the CDRs and any C-terminal extension that may be present) with the sequence of SEQ ID NO: 18 and/or 19.

The serum albumin binders according to the different aspects of the invention are generally preferably such that they bind to human serum albumin with a dissociation constant (KD) of $10^{-5}$ to $10^{-12}$ moles/liter or less, and preferably $10^{-7}$ to $10^{-12}$ moles/liter or less and more preferably $10^{-8}$ to $10^{-12}$ moles/liter, and/or with a binding affinity of at least $10^7$ $M^{-1}$, preferably at least $10^8$ $M^{-1}$, more preferably at least $10^9 M^{-1}$, such as at least $10^{12}$ $M^{-1}$, as determined using ProteOn (reference is made to Example 1). Preferably, a serum albumin binder of the invention will bind to the desired antigen with an affinity less than 500 nM, preferably less than 200 nM, more preferably less than 10 nM, such as less than 500 pM, again as determined using ProteOn (reference is again made to Example 1).

The serum albumin binders according to the different aspects of the invention are preferably also such that they compete with the amino acid sequence of SEQ ID NO:18 for binding to (human) serum albumin and/or that they "cross-block" (as defined herein) the binding of the amino acid sequence of SEQ ID NO:18 to (human) serum albumin.

Preferably, the albumin binders of the invention are such that they bind to essentially the same amino acid residues and/or epitope on human serum albumin as SEQ ID NO:18, and even more preferably such that they share essentially the same amino acid interactions SEQ ID NO:18. For this purpose, according to a specific but non-limiting aspect, the albumin binders of the invention preferably either have the same CDRs as the sequence of SEQ ID NO:18, or compared to the sequence of SEQ ID NO:18 preferably contain within their CDR's only such mutations (such as conservative amino acid substitutions) that still allow them to undergo the same or essentially the same amino acid interactions with human serum albumin as SEQ ID NO:18.

The serum albumin binders according to the different aspects of the invention are generally preferably also such that they are cross-reactive between human serum albumin and serum albumin from at least one, preferably from at least two, more preferably from at least three and up to essentially all of the following species of mammal: dog, rat, mouse, rabbit, guinea pig, pig, sheep, cow and cynomolgus monkey.

In particular, the serum albumin binders according to the different aspects of the invention are such that they are (at least) cross-reactive between human serum albumin and dog serum albumin, and preferably also between either human serum albumin and/or dog serum albumin on the one hand, and at least one, preferably at least two, more preferably at all three of rat serum albumin, mouse serum albumin and serum albumin from cynomolgus monkey on the other hand. In this respect, the serum albumin binders of the invention may have improved cross-reactivity (in particular between human serum albumin on the one hand and dog serum albumin on the other hand) compared to serum albumin binders that have (essentially) the same CDR's as Alb-11 and/or Alb-23D. Reference is made to the data in the Experimental Part below.

For the sake of reference, FIG. 11 gives an alignment of serum albumin from different species of mammal (source: http://macromoleculeinsights.com/albumin.php, the amino acid numbering in FIG. 11 is the numbering used on said webpage). For the sake of convenience, in the sequence of human serum albumin, the stretches of amino acids that are assumed to be part of the putative epitope of the amino acid sequences of the invention have been highlighted. Without being limited to any specific mechanism or hypothesis, it is assumed that the amino acid sequences of the invention are (essentially) capable of binding to (one or more amino acid residues within) the corresponding stretches of amino acid residues that are present within the amino acid sequence of those mammalian serum albumins that the amino acid sequences of the invention are cross-reactive with.

Generally, a serum albumin binder of the invention can be considered to be cross-reactive between human serum albumin and serum albumin from one of these species when it can bind to human serum albumin with an affinity less than 500 nM, preferably less than 200 nM, more preferably less than 10 nM; and also to the serum albumin from said species with an affinity less than 500 nM, preferably less than 200 nM, more preferably less than 10 nM, again both as determined using ProteOn (reference is again made to Example 1).

The serum albumin binders according to the different aspects of the invention are preferably also such that either:
they have a serum half-life in man (expressed as t1/2 beta) that is more than 6 hours, preferably more than 12 hours, more preferably of more than 24 hours, even more preferably more than 72 hours; for example of about one week, two weeks and up to the half-life of serum albumin in man (estimated to be around 19 days);
and/or such that:
when it is linked to a therapeutic moiety or entity, it confers to the resulting polypeptide of the invention a serum half-life in man (expressed as t1/2 beta) that is more than 6 hours, preferably more than 12 hours, more preferably of more than 24 hours, even more preferably more than 72 hours; for example of about one week, two weeks and up to the half-life of serum albumin in man (estimated to be around 19 days)

The half-life in mammalian species other than man will, among other factors, mainly depend on the binding properties (such as affinity) of the albumin binder of the invention for the serum albumin from said mammalian species as well on the half-life of the naïve serum albumin in said species. According to a preferred embodiment of the invention, when a serum albumin binder of the invention is cross-reactive (as defined herein) between human serum albumin and serum albumin from another mammalian species, then the half-life of the serum albumin binder of the invention (and/or of a compound of the invention comprising said serum albumin binder) as determined in said species is preferably at least 5%, such as at least 10%, more preferably at least 25%, for example about 50% and possibly up to 100% of the half-life of the naïve serum albumin in said species.

Compared to the sequence of SEQ ID NO:18, the serum albumin binders of the invention preferably also contain (at least):
one or more humanizing substitutions;
and/or
one or more mutations (i.e. amino acid substitutions, deletions or additions, and in particular substitutions) that reduce the binding by pre-existing antibodies;
and may optionally contain one or more further mutations as described herein.

For suitable humanizing substitutions (and suitable combinations thereof), reference is for example made to WO 09/138519 (or in the prior art cited in WO 09/138519) and WO 08/020079 (or in the prior art cited in WO 08/020079), as well as Tables A-3 to A-8 from WO 08/020079 (which are lists showing possible humanizing substitutions). Some preferred but non-limiting examples of such humanizing substitutions are Q108L and A14P or a suitable combination thereof. Such humanizing substitutions may also be suitably combined with one or more other mutations as described herein (such as with one or more mutations that reduce binding by pre-existing antibodies).

For suitable mutations that can reduce the binding by pre-existing antibodies (and suitable combinations of such mutations), reference is for example made to WO 2012/175741 and WO 2015/173325 and also to for example WO 2013/024059 and WO 2016/118733. As described therein, such mutations can comprise (a suitable combination of) one or more amino acid substitutions, deletions or additions (and in particular substitutions), which mutations will often be in the so-called C-terminal region of the ISV. For example, such mutations can comprise mutations (and in particular substitutions) at one or more of positions 11, 13, 14, 15, 40, 41, 42, 82, 82a, 82b, 83, 84, 85, 87, 88, 89, 103, 108 and/or mutations at one or more positions in the C-terminal VTVSS sequence (i.e. positions 109, 110, 111, 112 and 113), with one or more mutations at positions 11, 89, 110 and/or 112 being particularly preferred. Some preferred but non-limiting examples of such mutations are suitable substitutions (where required) such that after the mutation, at the indicated position, one of the following amino acid residues is present: 11L, 11K, 11V, 14A, 14P, 41A, 41L, 41P, 41S, 41T, 42E, 42G, 87A, 87T, 89A, 89L, 89T, 108L, 110K, 110Q, 112K and/or 112Q (with 11L, 89A, 89L, 89T, 110K, 110Q, 112K and 112Q being particularly preferred); or any suitable combination of such substitutions, such as for example and without limitation: 11V in combination with 89L or 89T; 11V in combination with 110K or 110Q; or 11V in combination with 89L and 110K or 110Q. Such mutations that reduce binding by pre-existing antibodies may also be suitably combined with one or more other mutations as described herein (such as with one or more humanizing substitutions).

Where appropriate (as further described herein, and in particular when the serum albumin binder of the invention is present at and/or forms the C-terminal end of the compound of the invention in which it is present), for reducing the binding of pre-existing antibodies, the serum albumin binders of the invention (and, as further described herein, also the compounds of invention) may also comprise a C-terminal extension (such as a C-terminal alanine residue). As described in WO 2012/175741, such a C-terminal extension reduces binding by pre-existing antibodies. A suitable C-terminal extension can generally be further described herein and can in particular have the formula —(X)$_n$, in which X can be any naturally occurring amino acid (but preferably not cysteine) and n can be 1, 2, 3, 4 or 5. Reference is again made to WO 2012/175741, to also to for example WO 2015/173325, WO 2013/024059 and WO 2016/118733. The presence of such a C-terminal extension may also be suitably combined with one or more of the other mutations described herein (such as with one or more humanizing substitutions and/or one or more mutations that reduce binding by pre-existing antibodies).

Other mutations that may be present in the serum albumin binders of the invention for example and without limitation include one or more mutations (an in particular substitutions) that improve expression in a desired host cell or host organism, one or more mutations (and in particular substitutions) that improve stability and/or resistance to degradation and/or proteases, and/or one or more other mutations that are intended to optimize the sequence of the amino acid sequences of the invention (for example and without limitation, one or more mutations that (further) reduce any tendency of the albumin binders to form dimers); or any suitable combination of such mutations.

Some non-limiting examples of such mutations are suitable substitutions (where required) such that after the mutation, at the indicated position, one of the following amino acid residues is present: 16G, 49A, 61D, 74S, 75K, 76N, 82M and 83R; or any suitable combination of such substitutions (for example so as to form an SKN motif at positions 74-76). Also, where appropriate (as further described herein), the serum albumin binders of the invention may have a D at position 1 (i.e. a E1D mutation compared to the sequence of SEQ ID NO:18 and/or 19), in particular when the serum albumin binder of the invention is present at and/or forms the N-terminal end of the compound of the invention in which it is present. Such mutations may again be suitably combined with one or more other mutations as described herein (such as with one or more humanizing substitutions and/or one or more mutations that reduce binding by pre-existing antibodies).

Other mutations that may be present in the amino acid sequences of the invention will be clear to the skilled person based on the disclosure herein.

It is also possible that a single mutation (or a suitable combination of mutations) provides multiple functionalities or advantages. For example and without limitation, a humanizing Q108L substitution may also reduce binding by pre-existing antibodies.

Some preferred but non-limiting examples of amino acid residues (i.e. mutations compared to the amino acid sequence of SEQ ID NO:18) that may be present in the amino acid sequences of the invention (i.e. by themselves or in suitable combination) include: 11V (i.e. L11V), 14P (i.e. A14P), 16G (i.e. D16G), 49A (i.e. S49A), 61D (i.e. N61D), 74S (i.e. D74S), 82M (i.e. L82M), 83R (i.e. K83R), 89L (i.e. V89L), 89T (i.e. V89T), 110K (e.g. T110K) or 110Q (e.g. T110Q); as well as, where appropriate (as further described herein), 1D (e.g. E1D) and/or a C-terminal extension (X)$_n$ as defined herein (such as 114A). Reference is also made to sequences and mutations shown in FIGS. 4A and 4B. For example, some preferred but non-limiting examples of suitable combinations of such amino acid residues (i.e. mutations compared to the amino acid sequence of SEQ ID NO:18) include:

L11V,T14P,D16G,N61D,D74S,K83R,V89L
L11V,T14P,D16G,D74S,L82M,K83R,V89L
L11V,T14P,D16G,N61D,D74S,L82M,K83R,V89L
L11V,T14P,D16G,S49A,D74S,K83R,V89L
L11V,T14P,D16G,S49A,N61D,D74S,K83R,V89L
L11V,T14P,D16G,S49A,D74S,L82M,K83R,V89L
L11V,T14P,D16G,S49A,N61D,D74S,L82M,K83R,V89L
L11V,T14P,D74S,K83R,V89L and other suitable combinations will be clear to the skilled person based on the disclosure herein.

Some preferred but non-limiting amino acid sequences of the invention are those in which (i) position 11 is V and position 89 is L; (ii) position 89 is T; (iii) positions 74-76 form an SKN motif; (iv) position 11 is V, position 89 is L and positions 74-76 form an SKN motif; and (iv) position 89 is T and positions 74-76 form an SKN motif; which amino acid sequences of the invention are as further described herein (and accordingly can also suitably contain one or more further amino acid mutations as described herein).

Some preferred, but non-limiting examples of the amino acid sequences of the invention are given in FIG. 2 as:
  SEQ ID NOs: 18 to 26, which are examples of amino acid sequences of the invention without a C-terminal alanine extension;
  SEQ ID NOs: 27 to 35, which are examples of amino acid sequences of the invention with a C-terminal extension (in each case, exemplified by means of a C-terminal alanine extension, which is generally the preferred C-terminal extension); and
  SEQ ID NOs: 36 to 44, which are examples of amino acid sequences of the invention with an N-terminal E1D mutation).

Based on the further disclosure herein, it will be clear to the skilled person that in practice:
  albumin binders of the invention with a C-terminal extension (such as those of SEQ ID NOs: 27 to 35) will often be used as/present at the C-terminal end of the polypeptides of the invention (as defined herein) in which they are present;
  albumin binders of the invention with an E1D mutation (such as those of SEQ ID NOs: 36 to 44) will often be used as/present at the N-terminal end of the polypeptides of the invention in which they are present;
  albumin binders of the invention without a C-terminal extension and without an E1D mutation (such as those of SEQ ID NOs: 18 to 26) will often be present somewhere in the "middle" of a polypeptide of the invention.

Each of the amino acid sequences of SEQ ID NOs: 18 to 44, as well as proteins, polypeptides and other compounds and constructs comprising the same (as further described herein), form further aspects of the present invention.

In a further aspect, the invention relates to an amino acid sequence which is one of the amino acid sequences of SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, and/or SEQ ID NO:44; and each of these amino acid sequences of the invention (as well as polypeptides of the invention—as defined herein—that comprise such an amino acid sequence of the invention) forms a further aspect of the present invention.

As further described herein, the amino acid sequences provided by the invention are proteins that can bind to, and that can in particular specifically (as described herein) bind to, human serum albumin. Thus, they can be used as binding units or binding domains for binding to (human) serum albumin, for example to confer an increase in half-life (as defined herein) to therapeutic compounds, moieties or entities. For the use of serum albumin-binding domains to increase half-life of therapeutic compounds, moieties or entities, reference is for example made to WO 2004/041865, WO 2006/122787, EP 2 139 918, WO 2011/006915, WO 2012/175400 and/or WO 2014/111550. The serum albumin binders of the invention can generally be used in the same way and for the same purposes as the serum albumin binders described in these references.

In some further non-limiting aspects, the invention also relates to:
- proteins, polypeptides and other constructs, molecules or chemical entities that comprise or essentially consist of at least one serum albumin binder of the invention as described herein (again, also referred to herein as "compounds of the invention" or as "polypeptides of the invention");
- methods for expressing/producing a serum albumin binder of the invention and/or a compound of the invention;
- a host cell, host organism or other (expression) system that can express or produce a serum albumin binder of the invention and/or a compound of the invention;
- compositions and products (such as pharmaceutical compositions and products) that comprise a serum albumin binder of the invention and/or a compound of the invention;
- nucleotide sequences and nucleic acids, such as (expression) vectors, that encode a serum albumin binder of the invention and/or a compounds of the invention;
- uses of the compounds of the invention and/or the compounds of the invention, such as the use of a compound of the invention to increase the (serum) half-life of a therapeutic compounds, moiety or entity and the therapeutic and/or prophylactic use of a compound of the invention.

These and further aspects, embodiments, advantages, applications and uses of the invention will become clear from the further description herein.

In the present specification:
- the term "immunoglobulin single variable domain" (also referred to as "ISV" or "ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VHs), IgNAR, domains, (single domain) antibodies (such as dAbs™) that are VH domains or that are derived from a VH domain and (single domain) antibodies (such as dAbs™) that are VL domains or that are derived from a VL domain. Unless explicitly mentioned otherwise herein, ISVDs that are based on and/or derived from heavy chain variable domains (such as VH or VHH domains) are generally preferred. Most preferably, unless explicitly indicated otherwise herein, an ISVD will be a Nanobody.
- the term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);
- Generally, unless indicated otherwise herein, the ISVD's, Nanobodies, polypeptides, proteins and other compounds and constructs referred to herein will be intended for use in prophylaxis or treatment of diseases or disorders in man (and/or optionally also in warm-blooded animals and in particular mammals). Thus, generally, the ISVD's, Nanobodies, polypeptides, proteins and other compounds and constructs described herein are preferably such that they can be used as, and/or can suitably be a part of, a (biological) drug or other pharmaceutically or therapeutically active compound and/or of a pharmaceutical product or composition. Such a drug, compound or product is preferably such that it is suitable for administration to a human being, e.g. for prophylaxis or treatment of a subject in need of such prophylaxis or treatment or for example as part of a clinical trial. As further described herein, for this purpose, such a drug or compound may contain other moieties, entities or binding units besides the ISVDs provided by the invention (which, as also described herein, may for example be one or more other further therapeutic moieties and/or one or more other moieties that influence the pharmacokinetic or pharmacodynamic properties of the ISVD-based or Nanobody-based biological, such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO 2009/138159. An ISVD-based biological or Nanobody-based biological is preferably a therapeutic or intended for use as a therapeutic (which includes prophylaxis and diagnosis) and for this purpose preferably contains at least one ISVD against a therapeutically relevant target (such as for example RANK-L, vWF, IgE, RSV, CXCR4, IL-23 or other interleukins, etc.). For some specific but non-limiting examples of such ISVD-based or Nanobody-based biologicals, reference is to Examples 8 to 18 and also for example made to the various applications by Ablynx N.V. (such as for example and without limitation WO 2004/062551, WO 2006/122825, WO 2008/020079 and WO 2009/068627), as well as for example (and without limitation) to applications such as WO 2006/038027, WO 2006/059108, WO 2007/063308, WO 2007/063311, WO 2007/066016 and WO 2007/085814. Also, as further described herein, the further moiety may be an ISVD or Nanobody as described herein directed against a (human) serum protein such as (human) serum albumin, and such an ISVD or Nanobody may also find therapeutic uses, in particular in and/or for extending the half-life of the TNF binders described herein. Reference is for example made to WO 2004/041865, WO 2006/122787 and WO 2012/175400, which generally describe the use of serum-albumin binding Nanobodies for half-life extension. Also, in the present specification, unless explicitly mentioned otherwise herein, all terms mentioned herein have the meaning given in WO 2009/138519 (or in the prior art cited in WO 2009/138519) or WO 2008/020079 (or in the prior art cited in WO 2008/020079). Also, where a method or technique is not specifically described herein, it can be performed as described in WO 2009/138519 (or in the prior art cited in WO 2009/138519) or WO 2008/020079 (or in the prior art cited in WO 2008/020079). Also, as described herein, any pharmaceutical product or composition comprising any ISVD or compound of the invention may also comprise one or more further components known per se for use in pharmaceutical products or compositions (i.e. depending on the intended pharmaceutical form) and/or for example one or more other compounds or active principles intended for therapeutic use (i.e. to provide a combination product).

Also, when used in the present specification or claims, the following terms have the same meaning as given on, and/or where applicable can be determined in the manner described in, pages 62-75 of WO 2009/138519: "agonist", "antagonist", "inverse agonist", "non polar, uncharged amino acid residue", "polar, uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 2010/130832 of Ablynx N.V. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 2009/138519, WO 2010/130832 or WO 2008/020079.

The term "half-life" as used herein in relation to an ISVD, Nanobody, ISVD-based biological, Nanobody-based biological or any other amino acid sequence, compound or polypeptide referred to herein can generally be defined as described in paragraph o) on page 57 of WO 2008/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO 2008/020079, the half-life can be expressed using parameters such as the t1/2-alpha, t1/2-beta and the area under the curve (AUC). In this respect it should be noted that the term "half-life" as used herein in particular refers to the t1/2-beta or terminal half-life (in which the t1/2-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/020079 and in particular refer to an increase in the t1/2-beta, either with or without an increase in the t1/2-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, N.Y. (2005), as well as to the general background art cited herein.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

As further described herein, the serum albumin binders of the invention can be used with advantage as a moiety, binding unit or fusion partner in order to increase the half-life of therapeutic compounds, moieties or entities such as polypeptides, proteins, compounds (including, without limitation, small molecules) or other therapeutic entities.

Thus, in another aspect, the invention provides polypeptides, proteins, compounds or other chemical entities that comprise or essentially consist of a serum albumin binder of the invention and one or more other amino acid sequences, (binding) domains, binding units or other moieties or chemical entities.

In particular, the invention provides polypeptides, proteins, constructs, compounds or other chemical entities that comprise a serum albumin binder of the invention and one or more (such as one or two) therapeutic moieties (which may be the same or different, and may for example be directed against the same target or to different targets, and when they are directed to the same target may be directed towards the same or different epitopes, parts, domains or subunits of said target), suitably linked to each other either directly or via one or more suitable linkers or spacers. Such polypeptides, proteins or constructs may for example and without limitation be a fusion protein, as further described herein.

The invention further relates to therapeutic uses of such polypeptides, proteins, constructs or compounds and to pharmaceutical compositions comprising such polypeptides, proteins, constructs or compounds.

In one aspect, the at least one therapeutic moiety comprises or essentially consists of a therapeutic protein, polypeptide, compound, factor or other entity. In a preferred embodiment the therapeutic moiety is directed against a desired antigen or target, is capable of binding to a desired antigen (and in particular capable of specifically binding to a desired antigen), and/or is capable of interacting with a desired target. In another embodiment, the at least one therapeutic moiety comprises or essentially consists of a therapeutic protein or polypeptide. In a further embodiment, the at least one therapeutic moiety comprises or essentially consists of a binding domain or binding unit, such as an immunoglobulin or immunoglobulin sequence (including but not limited to a fragment of an immunoglobulin), such as an antibody or an antibody fragment (including but not limited to an ScFv fragment), or of another suitable protein scaffold, such as protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

In yet another aspect, the at least one therapeutic moiety comprises or essentially consists of an antibody variable domain, such as a heavy chain variable domain or a light chain variable domain.

In a preferred aspect, the at least one therapeutic moiety comprises or essentially consists of at least one immunoglobulin single variable domain, such as a domain antibody, single domain antibody, "dAb" or Nanobody (such as a VHH, a humanized VHH or a camelized VH) or an IgNAR domain.

In a specific embodiment, the at least one therapeutic moiety comprises or essentially consists of at least one monovalent Nanobody or a bivalent, multivalent, bispecific or multispecific Nanobody construct.

The polypeptides, (fusion) proteins, constructs or compounds that comprise a serum albumin binder of the invention and one or more therapeutic moieties can generally be (prepared and used) as described in the prior art cited above (such as WO 04/041865, WO 06/122787, WO 2012/175400 and WO 2015/173325; reference is also made to for example, WO 2004/003019, EP 2 139 918, WO 2011/006915 and WO 2014/111550) with a serum albumin binder of the invention instead of the half-life increasing moieties described in said The polypeptides, (fusion) proteins, constructs or compounds that comprise a serum albumin binder of the invention and one or more therapeutic moieties will generally and preferably have an increased half-life (as described herein, and preferably expressed as t1/2-beta), compared to the therapeutic moiety or moieties per se.

Generally, the compounds, polypeptides, constructs or fusion proteins described herein preferably have a half-life (again, as described herein, and preferably expressed as t1/2-beta) that is at least 1.5 times, preferably at least 2 times, such as at least 5 times, for example at least 10 times or more than 20 times, greater than the half-life of the corresponding therapeutic moiety per se (as measured in either in man or a suitable animal, such as mouse or cynomolgus monkey).

Also, preferably, any such compound, polypeptide, fusion protein or construct has a half-life (again, as described herein, and preferably expressed as t1/2-beta) in man that is increased with more than 1 hour, preferably more than 2 hours, more preferably of more than 6 hours, such as of more than 12 hours, compared to the half-life of the corresponding therapeutic moiety per se.

Also, preferably, a compound or polypeptide of the invention has a half-life (again, as described herein, and preferably expressed as t1/2-beta) in man that is more than 1 hour, preferably more than 2 hours, more preferably of more than 6 hours, such as of more than 12 hours, and for example of about one day, two days, one week, two weeks and up to the half-life of serum albumin in man (estimated to be around 19 days).

As mentioned, in one aspect, a serum albumin binder of the invention is used to increase the half-life of (one or more) immunoglobulin single variable domains, such as domain antibodies, single domain antibodies, "dAb's", VHH's or Nanobodies (such as VHH's, humanized VHH's or camelized VH's such as camelized human VH's).

Thus, one embodiment of the invention relates to a polypeptide, construct or fusion protein that comprises a serum albumin binder of the invention and one or more (such as one or two) immunoglobulin single variable domain sequences, which are suitably linked to each other, either directly or optionally via one or more suitable linkers or spacers. As mentioned herein, each such immunoglobulin single variable domain present in such a polypeptide, construct or fusion protein may independently be a domain antibody, single domain antibody, "dAb" or Nanobody (such as a VHH, humanized VHH or camelized VH, such as a camelized human VH); and according to one specific but non-limiting aspect, at least one (and up to all) of these immunoglobulin single variable domains comprises two or three disulphide bridges. Preferably, all ISVDs present in such a compound of the invention are Nanobodies.

When a compound of the invention has an ISVD at its C-terminal end (such as a serum albumin binder of the invention or an ISVD that is directed against a therapeutic target), then said C-terminal ISVD (and thus, by extension, the entire compound of the invention) preferably has a C-terminal extension at its C-terminal end. This C-terminal extension will be directly linked to the last C-terminal amino acid residue of the ISVD, which will usually be the amino acid residue at position 113 according to Kabat (unless the ISVD contains one or more amino acid deletions such that the sequence of the ISVD ends before position 113). Thus, generally, the C-terminal extension will be directly linked to the C-terminal VTVSS sequence (SEQ ID NO:15) of the C-terminal ISV (and thus, by extension, to the C-terminal TVTSS sequence of the compound of the invention) or the C-terminal sequence of the C-terminal ISVD that corresponds to the C-terminal ISVD sequence (for example, where said C-terminal sequence of the C-terminal ISVD contains one or more substitutions or deletions compared to the usual VTVSS sequence, such as T110K, T110Q, S112K or S112K).

It will also be clear to the skilled person in the case where a compound of the invention has a serum albumin binder of the invention at its C-terminal end, that then said serum albumin binder of the invention will carry said C-terminal extension.

Generally, any C-terminal extension that is used herein (i.e. at the C-terminal end of a compound of the invention and/or at the C-terminal end of a serum albumin binder of the invention) can generally be as described in WO 2012/174741 or WO 2015/173325 (reference is also made to for example WO 2103/024059 and WO2016/118733). In particular, a C-terminal extension may have the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting aspects of such C-terminal extensions $X_{(n)}$, X and n can be as follows:
(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);
with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a serum albumin binder of the invention does not contain a (free) cysteine residue (unless said cysteine residue is used or intended for further functionalization, for example for pegylation).

Some specific, but non-limiting examples of useful C-terminal extensions are the following amino acid sequences: A, AA, AAA, G, GG, GGG, AG, GA, AAG, AGG, AGA, GGA, GAA or GAG.

Preferably also, when a compound of the invention has an ISVD at its C-terminal end (such as a serum albumin binder of the invention or an ISVD that is directed against a therapeutic target), then (at least) said C-terminal ISVD preferably contains, even more preferably in addition to a C-terminal extension as described herein, one or more mutations that reduce binding by pre-existing antibodies (i.e. as described herein for the serum albumin binders of the invention and as more generally described in WO 2012/175741 and WO 2015/173325 and also for example in WO 2013/024059 and WO 2016/118733). In this respect, it will be clear to the skilled person in the case where a compound of the invention has a serum albumin binder of the invention at its C-terminal end, that then (at least) said serum albumin binder of the invention preferably will contain such mutations (i.e. preferably in addition to a C-terminal extension).

More generally, according to a specific aspect of the invention, when a compound of the invention contains two or more ISVDs (e.g. a serum albumin binder of the invention and one or more ISVDs against a therapeutic target), then preferably all these ISVDs contain mutations that reduce binding to pre-existing antibodies (again, preferably in addition to the C-terminal extension that is linked to the C-terminal ISVD if the compound of the invention has an ISVD at its C-terminal end).

When a compound of the invention has an ISVD at its N-terminal end (such as a serum albumin binder of the invention or an ISVD that is directed against a therapeutic target), then said N-terminal ISVD (and thus, by extension, the entire compound of the invention) preferably contain a D at position 1. In this respect, it will again be clear to the skilled person in the case where a compound of the invention has a serum albumin binder of the invention at its N-terminal end, that then said serum albumin binder of the invention will preferably have a D at position 1 (e.g. an E1D mutation compared to for example the sequence of SEQ ID NO:18 and/or 19, such as the in the amino acid sequences of the invention of SEQ ID NOs: 36 to 44).

In some further aspects, the invention relates to a protein, polypeptide or other compound or construct that comprises or essentially consists of at least one (and preferably only one) serum albumin binder of the invention and at least one (such as one, two or three) therapeutic moiety or entity (in which said serum albumin binder and the one or more therapeutic moieties or entities are suitably linked, optionally via one or more suitable linkers), which protein, polypeptide, compound, construct is such that:

when it has an ISVD at its C-terminal end, then (the C-terminal ISVD of) said protein, polypeptide, compound, construct has a C-terminal extension (X). (as further described herein) at its C-terminal end; and/or when it has an ISVD at its C-terminal end, then at least said the C-terminal ISVD contains one or more mutations that reduce the binding of pre-existing antibodies (as further described herein);

when it has an ISVD at its N-terminal end, then (the N-terminal ISVD of) said protein, polypeptide, compound, construct preferably contains a D at position 1; and/or in which said ISVDs which protein, polypeptide or other compound may also have ISVD at its N-terminal end, in which case said N-terminal ISVD end preferably has a D or an E1D at position 1;

preferably, essentially all of the ISVDs present in said protein, polypeptide, compound, construct contain one or more mutations that reduce the binding of pre-existing antibodies (as further described herein).

According to one specific aspect of the invention, all therapeutic moieties present in a compound of the invention are ISVD's (i.e. ISVDs against a therapeutic target), and in particular heavy-chain ISVDs, and more in particular Nanobodies (i.e. Nanobodies against a therapeutic target).

For example and without limitation, such compounds of the invention may comprise:

one copy of a serum albumin binder of the invention and one ISVD (and preferably Nanobody) against a therapeutic target; or one copy of a serum albumin binder of the invention and two ISVDs (and preferably two Nanobodies) against a therapeutic target (which ISVDs may be the same or different and when different may be directed against the same target, against different epitopes on the same target or against different therapeutic targets); or one copy of a serum albumin binder of the invention and three ISVDs (and preferably three Nanobodies) against a therapeutic target (which ISVDs may be the same or different and when different may be directed against the same target, against different epitopes on the same target or against different therapeutic targets).

Some non-limiting examples of constructs, fusion proteins or polypeptides of the invention can be schematically represented as follows, in which "[Alb]" represents a serum albumin binder of the invention, "[therapeutic moiety 1]" and "[therapeutic moiety 2]" represent the therapeutic moieties (which as mentioned may each independently be an immunoglobulin single variable domain), "-" represents a suitable linker (which is optional; suitable examples are 9GS and 35GS linkers) and the N-terminus is on the left hand side and the C-terminus is on the right hand side:

[Alb]-[therapeutic moiety 1]
[therapeutic moiety 1]-[Alb]-$X_{(n)}$
[Alb]-[therapeutic moiety 1]-[therapeutic moiety 1]
[therapeutic moiety 1]-[therapeutic moiety 1]-[Alb]-$X_{(n)}$
[therapeutic moiety 1]-[Alb]-[therapeutic moiety 1]
[Alb]-[therapeutic moiety 1]-[therapeutic moiety 2]
[therapeutic moiety 1]-[therapeutic moiety 2]-[Alb]-$X_{(n)}$
[therapeutic moiety 1]-[Alb]-[therapeutic moiety 2]

When the therapeutic moieties are ISVDs (and preferably Nanobodies) against a therapeutic target, preferred but non-limiting constructs, fusion proteins or polypeptides of the invention can be schematically represented as follows, in which "[Alb]" represents a serum albumin binder of the invention, "[therapeutic ISVD 1]" and "[therapeutic ISVD 2]" represent ISVDs against a therapeutic target (which ISVDs may be the same or different and when different may be directed against the same target, against different epitopes on the same target or against different therapeutic targets), "-" represents a suitable linker (which is optional), X(n) represents a C-terminal extension as described herein, and the N-terminus is on the left hand side and the C-terminus is on the right hand side:

[Alb]-[therapeutic ISVD 1]-$X_{(n)}$
[therapeutic ISVD 1]-[Alb]-$X_{(n)}$
[Alb]-[therapeutic ISVD 1]-[therapeutic ISVD 1]-$X_{(n)}$
[therapeutic ISVD 1]-[therapeutic ISVD 1]-[Alb]-$X_{(n)}$
[therapeutic ISVD 1]-[Alb]-[therapeutic ISVD 1]-$X_{(n)}$
[Alb]-[therapeutic ISVD 1]-[therapeutic ISVD 2]-$X_{(n)}$
[therapeutic ISVD 1]-[therapeutic ISVD 2]-[Alb]-$X_{(n)}$
[therapeutic ISVD 1]-[Alb]-[therapeutic ISVD 2]-$X_{(n)}$ Thus, in another aspect, the invention relates to a multi-specific (and in particular bispecific) Nanobody construct that comprises a serum albumin binder of the invention and at least one other Nanobody (such as one or two other Nanobodies, which may be the same or different), in which said at least one other Nanobody is preferably directed against a desired target (which is preferably a therapeutic target) and/or another Nanobody that useful or suitable for therapeutic, prophylactic and/or diagnostic purposes. Again, the serum albumin binder of the invention and the other Nanobodies may be suitably linked to each other either directly or optionally via one or more suitable linkers or spacers.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103, WO 99/23221, WO 04/041862, WO 2006/122786, WO 2008/020079, WO 2008/142164 or WO 2009/068627.

By means of illustration, some examples of compounds of the invention are given in SEQ ID NOs:46 to 52, using the anti-HER2-Nanobody of SEQ ID NO: 45 as a representative example of an anti-target Nanobody, and with the constituent Nanobodies being in different positions in the compound of the invention. The compounds of SEQ ID NOs: 46 to 49 are examples illustrating bivalent bispecific compounds of the invention and the compounds of SEQ ID NOs: 50 to 52 are examples illustrating trivalent bispecific compounds of the invention. In each case, the compounds contain an E1D mutation and a C-terminal alanine residue, and contain representative but non-limiting examples of the use of suitable linkers (i.e. a 15GS linker in SEQ ID NOs:47 and 48 and or 35GS linkers in SEQ ID NO:s 46 and 49 to 52).

Some other examples of some specific multispecific and/or multivalent polypeptide of the invention can be found in the applications by Ablynx N.V. mentioned herein. In particular, for a general description of multivalent and multispecific constructs comprising at least one Nanobody against a serum protein for increasing the half-life, of nucleic acids encoding the same, of compositions comprising the same, of the preparation of the aforementioned, and of uses of the aforementioned, reference is made to the International applications WO 04/041865 and WO 06/122787 mentioned above (the serum albumin binders of the invention described herein can generally be used analogously to the half-life extending Nanobodies described therein such as Alb-8), as well as to the general description and specific examples of such constructs given in for example WO 04/041862, WO 2006/122786, WO 2008/020079, WO 2008/142164 or WO 2009/068627.

The invention also relates to nucleotide sequences or nucleic acids that encode the albumin binders, compounds or polypeptides of the invention. The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V., such as for example WO 04/041862, WO 2006/122786, WO 2008/020079, WO 2008/142164 or WO 2009/068627.

The invention also relates to hosts or host cells that contain such nucleotide sequences or nucleic acids, and/or that express (or are capable of expressing), the albumin binders, compounds or polypeptides of the invention. Again, such host cells can be generally as described in the published patent applications of Ablynx N.V., such as for example WO 04/041862, WO 2006/122786, WO 2008/020079, WO 2008/142164 or WO 2009/068627.

The invention also relates to a method for preparing an albumin binder, compound or polypeptide of the invention, which method comprises cultivating or maintaining a host cell as described herein under conditions such that said host cell produces or expresses an albumin binder, compound or polypeptide of the invention, and optionally further comprises isolating the albumin binder, compound or polypeptide of the invention so produced. Again, such methods can be performed as generally described in the published patent applications of Ablynx N.V., such as for example WO 04/041862, WO 2006/122786, WO 2008/020079, WO 2008/142164 or WO 2009/068627.

The invention also relates to a pharmaceutical composition that comprises at least one compound or polypeptide of the invention, and optionally at least one pharmaceutically acceptable carrier, diluent or excipient. Such preparations, carriers, excipients and diluents may generally be as described in the published patent applications of Ablynx N.V., such as for example WO 04/041862, WO 2006/122786, WO 2008/020079, WO 2008/142164 or WO 2009/068627.

However, since the compounds or polypeptides of the invention have an increased half-life, they are preferably administered to the circulation. As such, they can be administered in any suitable manner that allows the compound or polypeptide of the invention to enter the circulation, such as intravenously, via injection or infusion, or in any other suitable manner (including oral administration, subcutaneous administration, intramuscular administration, administration through the skin, intranasal administration, administration via the lungs, etc.). Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

Thus, in another aspect, the invention relates to a method for the prevention and/or treatment of at least one disease or disorder that can be prevented or treated by the use of a compound or polypeptide of the invention, which method comprises administering, to a subject in need thereof, a pharmaceutically active amount of a compound or polypeptide of the invention, and/or of a pharmaceutical composition comprising the same. The diseases and disorders that can be prevented or treated by the use of a compound or polypeptide of the invention as described herein will generally be the same as the diseases and disorders that can be prevented or treated by the use of the therapeutic moiety or moieties that is/are present in the compound or polypeptide of the invention.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a compound or polypeptide of the invention, and/or of a pharmaceutical composition comprising the same.

The compound or polypeptide of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more compounds or polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency and/or the half-life of the compounds or polypeptides of the invention to be used, the specific route of administration and the specific pharmaceutical formulation or composition used, the compounds or polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Also, as the compounds of the invention contain a half-life extending serum albumin binder of the invention, they do not need to be administered essentially continuously (e.g. by infusion), but they can be administered at suitable intervals (to be determined by the skilled person). For example, they can be administered (at a suitable dose) once every two days, once every four days, once weekly, once every two weeks and in some cases once every four weeks or even less frequently, for example by injection or infusion.

One aspect of the invention relates to a pharmaceutical composition comprising at least one compound or polypeptide of the invention wherein said composition is intended for administration at an interval between once weekly and once every 4 weeks, and in particular between once every 7 days and once every 21 days, such as once every 7 days or 14 days.

Usually, in the above method, a single polypeptide of the invention will be used. It is however within the scope of the invention to use two or more polypeptides of the invention in combination.

The polypeptides of the invention may also be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides of the invention may be used in combination with other pharmaceutically active compounds or principles that are or can be used for the prevention and/or treatment of the diseases and disorders that can be prevented or treated with the fusion proteins or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Other aspects, embodiments, advantages and applications of the invention will become clear from the further description herein.

The invention will now be further described by means of the following non-limiting preferred aspects, examples and figures, in which:

FIG. 1 is a table listing some of the amino acid positions that will be specifically referred to herein and their numbering according to some alternative numbering systems (such as Aho and IMGT);

FIG. 2 lists the amino acid sequences referred to herein;

FIGS. 3A and 3B show an alignment of the sequences of SEQ ID NOs:18 and 19 (invention) with the prior art sequences of SEQ ID NOs: 1 and 2;

FIG. 5 gives an alignment of serum albumin from different species of mammal. Mouse: SEQ ID NO: 54; Rat: SEQ ID NO: 56; Dog: SEQ ID NO: 59; Cat: SEQ ID NO: 60; Human: SEQ ID NO: 54; Cow: SEQ ID NO: 57; Sheep: SEQ ID NO: 61; Pig: SEQ ID NO: 58; Horse: SEQ ID NO: 62; Rabbit: SEQ ID NO: 63.

Figure 4:
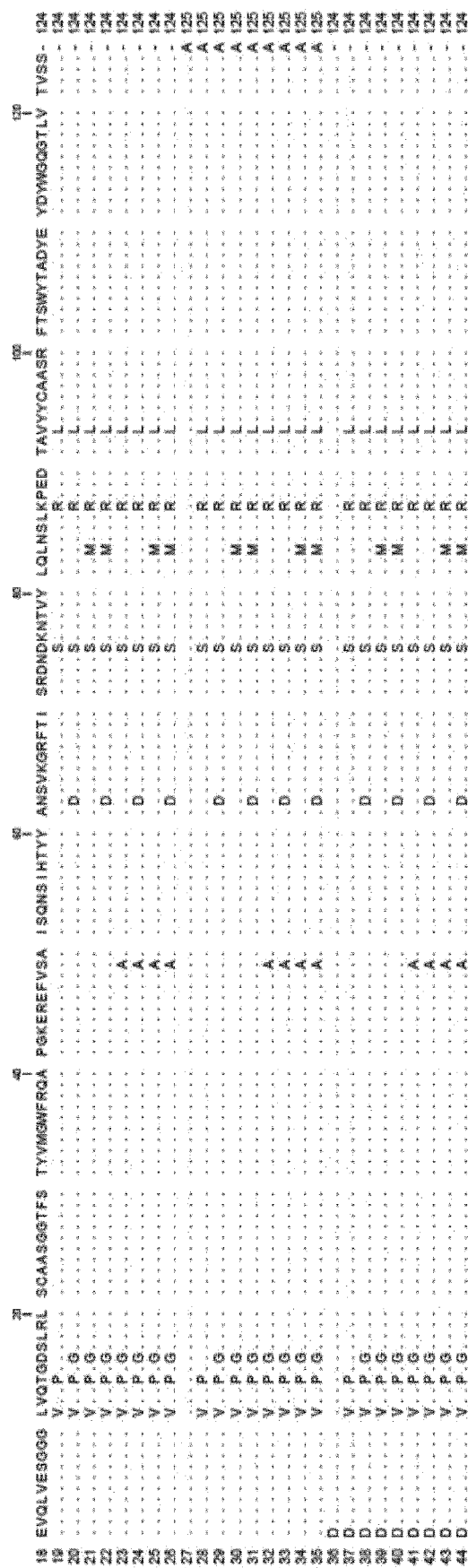
FIG. 4 shows an alignment of SEQ ID NOs: 18 to 44.
Figure 6:
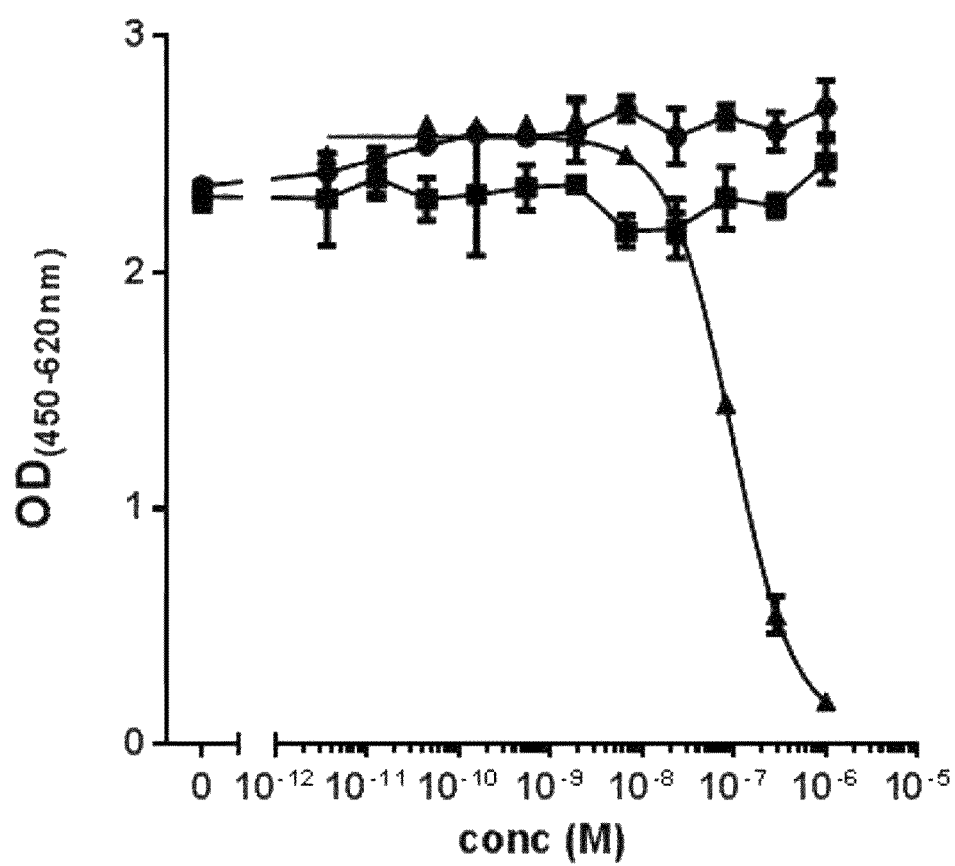

FIG. 6 is a graph showing binding of SEQ ID NO:1 (reference)-cMycHis6 to coated HSA in presence of the serum albumin binder of SEQ ID NO:19 (invention). 1.5 nM SEQ ID NO:1-cMycHis6 and concentration series of His6Flag3-SEQ ID NO:1 (reference), Flag3His6-SEQ ID NO:19 (invention) or cAblys3-Flag3His6 (reference) were incubated on coated HSA. Bound SEQ ID NO:1-cMycHis6 was detected with goat anti-cMyc and HRP-labelled rabbit anti-goat antibodies.

Figure 7:
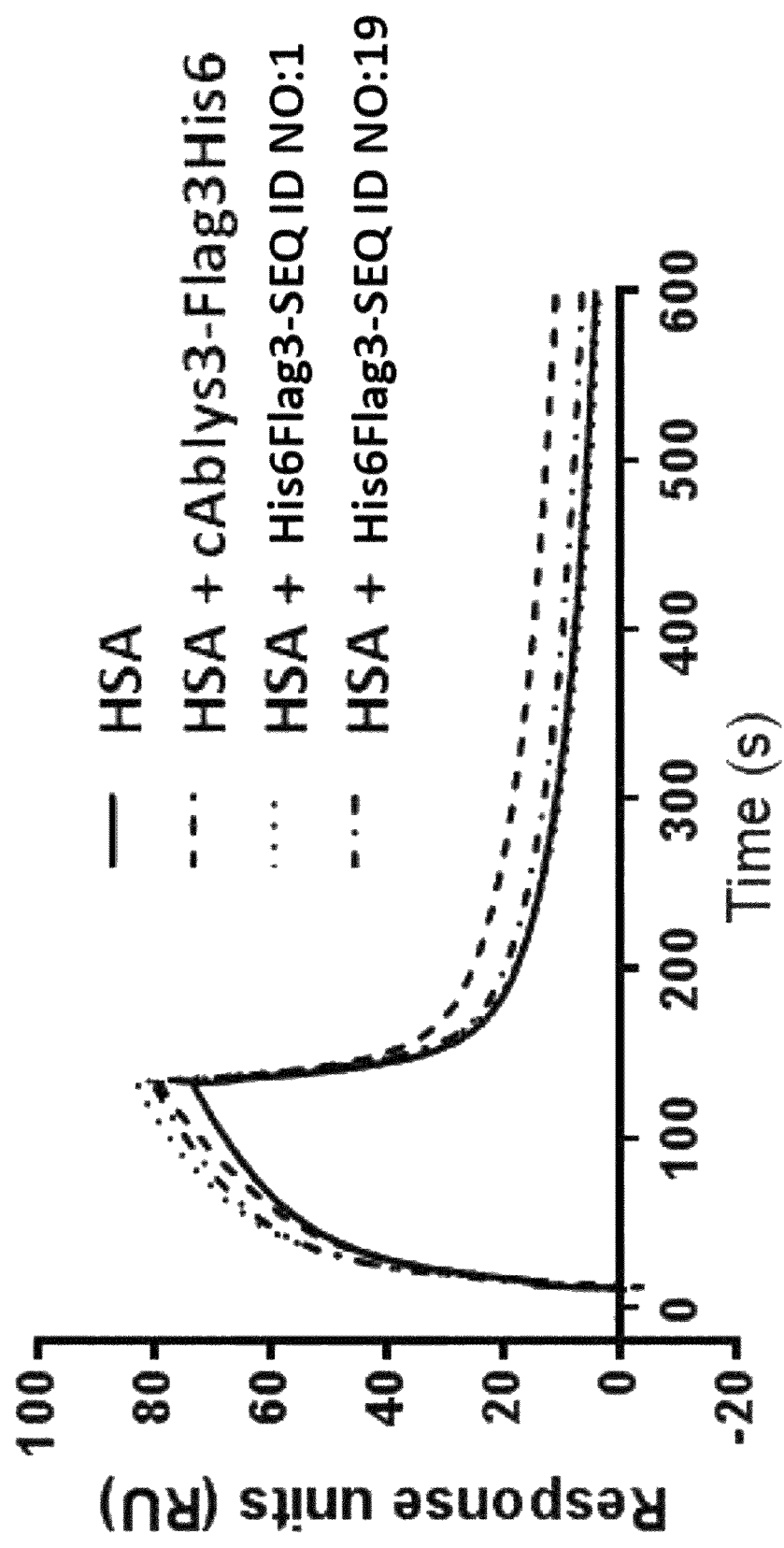

FIG. 7 is a graph showing binding of HSA to FcRn in presence of the serum albumin binder of SEQ ID NO:19 (invention). Human FcRn-human β2 microglobulin heterodimer was immobilized on CM5 chip. Binding of 1 μM HSA in absence or presence of 2 μM Nanobody in 50 mM NaPO4+150 mM NaCl+0.05% Tween-20 pH 6.0 was monitored on a Biacore T100 instrument.

The entire contents of all of the references (including literature references, issued patents, published patent applications, and co pending patent applications) cited throughout this application are hereby expressly incorporated by reference, in particular for the teaching that is referenced hereinabove.

EXPERIMENTAL PART

Example 1 Affinity for Serum Albumin

The affinity of the serum albumin binder of SEQ ID NO:19 (invention) for human (Sigma-Aldrich A3782), cynomolgus monkey (generated in-house), mouse (Albumin Bioscience 2601), rat (Sigma-Aldrich A4538), rabbit (Sigma-Aldrich A0764), guinea pig (Gentaur GPSA62), pig (Sigma-Aldrich A4414), sheep (Sigma-Aldrich A3264), dog (Abcam 119814) and bovine (Sigma-Aldrich A3059) serum albumin (SA) was measured via Surface Plasmon Resonance (SPR) on a ProteOn XPR36 (BioRad) instrument. Serum albumin was immobilized via amine coupling on GLC ProteOn chip using ProteOn Amine Coupling Kit (BioRad). Different concentrations (300 nM, 100 nM, 33.3 nM, 11.1 nM, 3.7 nM and 1.23 nM) of the serum albumin binder of SEQ ID NO:19 (invention) were injected in HBS-P+pH 7.4 buffer (GE Healthcare) at 45 µL/min for 120 s, followed by dissociation for 900 s. There was no or very low binding observed for the serum albumin binder of SEQ ID NO:19 (invention) on rabbit, sheep and bovine SA. The affinities of the serum albumin binder of SEQ ID NO:19 (invention) for human, cynomolgus monkey, rat, mouse and guinea pig SA were higher compared to the respective affinities of the albumin binder of SEQ ID NO:1. The results are given in Table 1 below and show that the serum albumin binder of SEQ ID NO:19 (invention) is cross-reactive with dog and pig SA.

TABLE 1

Kinetic parameters for binding of SEQ ID NO: 19 (invention) on SA from different species.

| | SEQ ID NO: 19 (invention) | | | SEQ ID NO: 1 (reference) | | |
|---|---|---|---|---|---|---|
| SA | ka ($s^{-1}M^{-1}$) | Kd ($s^{-1}$) | KD (M) | ka ($s^{-1}M^{-1}$) | Kd ($s^{-1}$) | KD (M) |
| human | 6.1E+05 | 2.7E−04 | 4.4E−10 | 4.9E+05 | 1.6E−03 | 3.3E−09 |
| cyno | 5.2E+05 | 2.3E−04 | 4.5E−10 | 4.6E+05 | 1.4E−03 | 3.1E−09 |
| rat | 1.2E+06 | 8.0E−05 | 6.7E−11 | 3.9E+05 | 2.6E−01 | 6.7E−07 |
| mouse | 9.1E+05 | 2.5E−04 | 2.7E−10 | 6.6E+05 | 3.0E−02 | 3.9E−08 |
| guinea pig | 1.0E+06 | 3.1E−04 | 3.0E−10 | 9.4E+05 | 1.9E−02 | 2.0E−08 |
| dog | 7.2E+05 | 8.4E−04 | 1.2E−09 | | no binding | |
| pig | 1.0E+05 | 4.6E−03 | 4.5E−08 | | no binding | |

The serum albumin binder of SEQ ID NO: 19 (invention) was injected at different concentrations on immobilized SA on a ProteOn instrument. Binding and dissociation kinetics were analysed at pH 7.4. Kinetic parameters for SEQ ID NO: 1 are listed as a reference and were determined in separate experiments.

The long half-life of albumin in blood is mainly driven by two characteristics: (i) the large size (65 kDa) of albumin limits its glomerular filtration and (ii) albumin binds to FcRn at low pH (pH 6), which protects albumin from degradation in the lysosomes after passive endocytosis in endothelial and epithelial cells, by recycling from early endosome back to the extracellular environment. For albumin-binding Nanobodies to result in long serum half-life through albumin binding and subsequent recycling, these should stay bound to albumin in the pH range from 5.0 to 7.4. The dissociation rate of the serum albumin binder of SEQ ID NO:19 (invention) from HSA at pH 5, pH 6 and pH 7.4 was measured on a ProteOn instrument as described above, including SEQ ID NO:1 (reference) as a reference. the serum albumin binder of SEQ ID NO:19 (invention) and SEQ ID NO:1 (reference) were injected at 500 nM and 300 nM respectively in HBS-P+pH 7.4 buffer. Dissociation buffers were 50 mM NaOAc/HOAc+150 mM NaCl+0.05% Tween-20 pH 5.0, 50 mM NaOAc/HOAc+150 mM NaCl+0.05% Tween-20 pH 6.0 and HBS-P+pH 7.4 respectively. Dissociation was analysed for 2700 s. Dissociation rates for the serum albumin binder of SEQ ID NO:19 (invention) do not differ significantly across the pH range from 5.0 to 7.4. The results are shown in Table 2.

TABLE 2

Dissociation rate of the serum albumin binder of SEQ ID NO: 19 (invention) from HSA at different pH.

| | kd ($s^{-1}$) | |
|---|---|---|
| pH | SEQ ID NO: 19 (invention) | SEQ ID NO: 1 (reference) |
| pH 7.4 | 2.0E−04 | 1.3E−03 |
| pH 6.0 | 3.2E−04 | 9.2E−04 |
| pH 5.0 | 5.1E−04 | 1.1E−03 |

The serum albumin binders of SEQ ID NO: 19 (invention) and SEQ ID NO: 1 (reference) were injected on immobilized HSA. Dissociation was monitored at pH 5.0, 6.0 and 7.4 on a ProteOn instrument.

Example 2 Epitope

Epitope binning was analysed in a competition ELISA. Human serum albumin was coated at 125 ng/ml in PBS at 4° C. overnight. After blocking with PBS+1% casein, 1.5 nM SEQ ID NO:1 (reference)-cMycHis6 and a concentration series of competitors (His6Flag3—the serum albumin binder of SEQ ID NO:19 (invention), His6Flag3-SEQ ID NO:1 (reference) as positive control or hen egg lysozyme binding single domain antibody cAblys3-Flag3His6 as negative control) were added. Bound SEQ ID NO:1 (reference)-cMycHis6 was detected with goat anti-cMyc (Abcam ab19234) and HRP-labelled rabbit anti-goat (Genway 18-511-244226) antibodies. The serum albumin binder of SEQ ID NO:19 (invention) and SEQ ID NO:1 (reference) do not bind identical epitopes on HSA (FIG. 6).

Example 3 Interference with Interaction Between SA and FcRn

For the serum albumin binder of SEQ ID NO:19 (invention) to result in long half-life via albumin binding and subsequent recycling, it should not interfere with the binding of albumin to FcRn. This was analysed in SPR on a Biacore T100 (GE Healthcare) instrument. Human FcRn-human β2 microglobulin heterodimer (Sino Biological CT009-H08H) was immobilized on CM5 chip via standard amine coupling (Biacore amine coupling kit). A mixture of 1 µM HSA and 2 µM Nanobody (His6Flag3—the serum albumin binder of SEQ ID NO:19 (invention), His6Flag3-SEQ ID NO:1 (reference) or cAblys3-Flag3His6) in 50 mM NaPO4+150 mM NaCl+0.05% Tween-20 pH 6.0 was injected at 10 µl/min for 120 s, followed by dissociation for 600 s. Binding curves were qualitatively compared with binding curve of 1 µM HSA in absence of Nanobody. the serum albumin binder of SEQ ID NO:19 (invention) did not interfere with the binding of HSA to FcRn (FIG. 7).

Example 4 PK Profile in Dog

Pharmacokinetics of a trivalent Nanobody construct (SEQ ID NO:53) after single i.v. dose are studied in dog. The trivalent construct was produced in *Pichia pastoris* and comprises two Nanobodies against respiratorial syncytial virus (RSV) with the albumin binding Nanobody of SEQ ID NO:21 at the C-terminal end (in which the three Nanobodies are linked to each other using (Gly4Ser)7 linkers).

The pharmacokinetic profile of the construct is evaluated in a pharmacokinetic study (non-crossover, single dose) in twelve fasted healthy male Beagle dogs (healthy as determined by a pre-study health examination). The construct is administered intravenously.

The animals are fasted (with uninterrupted access to water) overnight prior to dosing, and prior to collection of blood samples at pre-dose, 24, 168, and 336 hours after dosing (total fasting time no longer than 24 hours). Food is returned 4 hours post-dose, or immediately after blood collection at 24, 168, and 336 hours. Body weight is also recorded and tracked during the study.

1 ml of whole blood (or 2-3 ml pre-dose and at 24, 168 and 336 hours) for plasma is collected from a peripheral vessel pre-dose and at 5, 15, 30 min and 1, 4, 8, 12, 24, 72, 168, 240, 336, 504, and 672 hours post initial dose. Collected samples for serum processing are kept at room temperature and are allowed to clot. Blood is be centrifuged at 10,000 rpm for 2 minutes using a refrigerated centrifuge (set to maintain 4° C.). Samples are frozen within 30 minutes from collection until they are submitted for analysis (including measurement of concentration of the relevant Nanobody construct).

The invention claimed is:

1. An immunoglobulin single variable domain (ISVD) capable of binding to serum albumin that comprises:
   a CDR1 (according to Abm) that is the amino acid sequence GGTFSTYVMG (SEQ ID NO: 12); and
   a CDR2 (according to Abm) that is the amino acid sequence AISQNSIHTY (SEQ ID NO: 13); and
   a CDR3 (according to Abm) that is the amino acid sequence SRFTSWYTADYEYDY (SEQ ID NO: 14),
   optionally wherein the serum albumin is human serum albumin.

2. The ISVD according to claim 1, that can bind to human serum albumin with an affinity better than 100 nM or better than 50 nM, as determined by surface plasmon resonance.

3. The ISVD according to claim 1, that is a heavy-chain immunoglobulin single variable domain.

4. The ISVD according to claim 1, that is a VHH, a humanized VHH or a camelized VH, optionally wherein the camelized VH is a camelized human VH.

5. The ISVD according to claim 1, wherein
   the ISVD has a serum half-life in human (expressed as t1/2 beta) that is more than 6 hours, 12 hours, 24 hours, or 72 hours.

6. The ISVD according to claim 1, that has:
   a degree of sequence identity with the sequence of SEQ ID NO: 18 and/or 19 of at least 85%, at least 90%, or at least 95%;
   and/or that has:
   no more than 7, no more than 5, no more than 3, no more than 2, or no more than 1 amino acid differences with the sequence of SEQ ID NO: 18 or 19;
   wherein the CDRs are not taken into account for determining the degree of sequence identity or the amino acid differences.

7. The ISVD according to claim 1, that has:
   a degree of sequence identity with the sequence of SEQ ID NO: 18 of at least 85%, at least 90%, or at least 95%;
   or that has:
   no more than 7, no more than 5, no more than 3, no more than 2, or no more than 1 amino acid differences with the sequence of SEQ ID NO: 18;
   wherein the CDRs are not taken into account for determining the degree of sequence identity or the amino acid differences.

8. The ISVD according to claim 1, that has:
   a degree of sequence identity with the sequence of SEQ ID NO: 19 of at least 85%, at least 90%, or at least 95%;
   or that has:
   no more than 7, no more than 5, no more than 3, no more than 2, or no more than 1 amino acid differences with the sequence of SEQ ID NO: 19;
   wherein the CDRs are not taken into account for determining the degree of sequence identity or the amino acid differences.

9. The ISVD according to claim 1, that is a VHH and that contains, compared to the sequence of SEQ ID NO:18, one or more humanizing substitutions.

10. An immunoglobulin single variable (ISVD) domain capable of binding to serum albumin and that is chosen from SEQ ID NO's: 18 to 44, optionally wherein the serum albumin is human serum albumin.

11. A polypeptide that comprises at least one immunoglobulin single variable domain (ISVD) according to claim 1.

12. The polypeptide according to claim 11, that comprises at least one therapeutic moiety or entity.

13. The polypeptide according to claim 11, that is a fusion protein.

14. The polypeptide according to claim 11, that has a serum half-life in human (expressed as t1/2 beta) that is more than 6 hours, more than 12 hours, more than 24 hours, or than 72 hours.

15. The polypeptide according to claim 11, wherein:
   the polypeptide further comprises a C-terminal ISVD, wherein the C-terminal ISVD polypeptide comprises a C-terminal extension (X)n, wherein each X is an amino acid residue that is independently chosen from naturally occurring amino acid residues, and wherein n is 1-10; and/or
   the polypeptide further comprises a N-terminal ISVD, wherein the N-terminal ISVD polypeptide comprises a D at position 1.

16. A pharmaceutical composition comprising a polypeptide according to claim 11.

17. A nucleic acid that encodes an ISVD according to claim 1.

18. An expression vector that comprises the nucleic acid of claim 17.

19. A host cell that comprises an expression vector according to claim 18.

20. A method for preparing a polypeptide comprising cultivating or maintaining a host cell according to claim 19 under conditions such that said host cell produces or expresses the polypeptide, and optionally further comprising isolating the polypeptide.

21. The polypeptide according to claim 12, that has a serum half-life in human (expressed as t1/2 beta) that is more than 6 hours, more than 12 hours, more than 24 hours, or more than 72 hours.

22. The ISVD according to claim 1, wherein the ISVD cross-blocks the binding of the amino acid sequence of SEQ ID NO: 18 and/or SEQ ID NO: 19 to human serum albumin.

* * * * *

UNITED STATES PATENT AND TRADEMARK OFFICE
CERTIFICATE OF CORRECTION

PATENT NO. : 11,414,481 B2
APPLICATION NO. : 16/477918
DATED : August 16, 2022
INVENTOR(S) : Stephanie Staelens et al.

It is certified that error appears in the above-identified patent and that said Letters Patent is hereby corrected as shown below:

In the Claims

Claim 6, at Column 105, Lines 36-46, should read:
6. The ISVD according to claim 1, that has:
    a degree of sequence identity with the sequence of SEQ
        ID NO: 18 or 19 of at least 85%, at least 90%, or at
        least 95%;
or that has:
    no more than 7, no more than 5, no more than 3, no more
        than 2, or no more than 1 amino acid differences with
        the sequence of SEQ ID NO: 18 or 19;
    wherein the CDRs are not taken into account for
        determining the degree of sequence identity or the
        amino acid differences.

Signed and Sealed this
First Day of November, 2022

Katherine Kelly Vidal
*Director of the United States Patent and Trademark Office*